United States Patent
Pulugurtha et al.

(10) Patent No.: US 12,427,231 B2
(45) Date of Patent: Sep. 30, 2025

(54) PROTECTED MAGNESIUM ALLOYS FOR BIORESORBABLE STENTS

(71) Applicant: Medtronic Vascular, Inc., Santa Rosa, CA (US)

(72) Inventors: Syamala Rani Pulugurtha, Santa Rosa, CA (US); Jeffrey Allen, Santa Rosa, CA (US); James Mitchell, Santa Rosa, CA (US); Christopher Storment, Santa Rosa, CA (US); Jill Mendelson, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 17/941,851

(22) Filed: Sep. 9, 2022

(65) Prior Publication Data
US 2023/0001057 A1   Jan. 5, 2023

Related U.S. Application Data

(62) Division of application No. 16/442,740, filed on Jun. 17, 2019, now Pat. No. 11,517,649, which is a
(Continued)

(51) Int. Cl.
*A61F 2/915* (2013.01)
*A61F 2/89* (2013.01)
(Continued)

(52) U.S. Cl.
CPC ............. *A61L 31/088* (2013.01); *A61F 2/89* (2013.01); *A61F 2/915* (2013.01); *A61L 31/022* (2013.01);
(Continued)

(58) Field of Classification Search
CPC .. A61F 2002/91541; A61F 2002/91575; A61F 2210/0076; A61F 2230/0069; A61F 2/89; A61F 2/915; C23C 22/57
See application file for complete search history.

(56) References Cited

U.S. PATENT DOCUMENTS 8,636,792 B2   1/2014 Zheng et al.
2010/0305684 A1   12/2010 Kim et al.
(Continued)

FOREIGN PATENT DOCUMENTS

| WO | 2011/143263 | 11/2011 |
|----|-------------|---------|
| WO | 2013/116785 | 8/2013 |
| WO | 2014/110019 | 7/2014 |

OTHER PUBLICATIONS

Hornberger et al. "Biomedical Coatings on Magnesium Alloy", Acta Biomaterialia, vol. 8, Issue 7, pp. 2442-2455, Jul. 2012 ( Year: 2012).*
(Continued)

*Primary Examiner* — Lois L Zheng
(74) *Attorney, Agent, or Firm* — Mueting Raasch Group

(57) ABSTRACT

Biodegradable magnesium alloy implantable medical devices are protected to delay onset of corrosion, and thus biodegradability, or to corrode more uniformly. The protection allows for extended effective use of the devices while maintaining biodegradability. Examples of protective coatings include conversion coatings that at least partially remove exposed second phases from a surface of the magnesium alloy and coatings that provide a barrier between water and the surface of the magnesium alloy.

13 Claims, 11 Drawing Sheets

Related U.S. Application Data division of application No. 14/934,645, filed on Nov. 6, 2015, now Pat. No. 10,322,214.

(60) Provisional application No. 62/076,214, filed on Nov. 6, 2014.

(51) Int. Cl.
| | |
|---|---|
| *A61L 31/02* | (2006.01) |
| *A61L 31/08* | (2006.01) |
| *A61L 31/10* | (2006.01) |
| *A61L 31/14* | (2006.01) |
| *C23C 16/06* | (2006.01) |
| *C23C 22/57* | (2006.01) |
| *C23C 8/10* | (2006.01) |

(52) U.S. Cl.
CPC ............ *A61L 31/084* (2013.01); *A61L 31/10* (2013.01); *A61L 31/148* (2013.01); *C23C 16/06* (2013.01); *A61F 2002/91541* (2013.01); *A61F 2002/91575* (2013.01); *A61F 2210/0076* (2013.01); *A61F 2230/0069* (2013.01); *A61L 2420/02* (2013.01); *A61L 2420/08* (2013.01)

(56) References Cited

U.S. PATENT DOCUMENTS

| | | |
|---|---|---|
| 2012/0150286 A1 | 6/2012 | Weber et al. |
| 2014/0277396 A1 | 9/2014 | Mendelson et al. |

OTHER PUBLICATIONS

Lin, C.S. and Fang, S.K., "Formation of Cerium Conversion Coatings on AZ31 Magnesium Alloys," Journal of the Electrochemical Society, 2005. 152 (2):B54-B59.

Montemor, M.F., Ferreira, M.G.S. "Electrochemical study of bis-[triethoxysilylpropyl] tetrasulfide silane films applied on the AZ31 Mg alloy," Electrochimica Acta V.52 i:27 p. 7486-7495 Oct. 10, 2007.

Ng, W.F., Wong, M.H., and Cheng, F.T. "Cerium-based coating for enhancing the corrosion resistance of bio-degradable Mg implants," Materials Chemistry and Physics, 2010. 119:384-388.

PCT/US2016/017743, The International Search Report and The Written Opinion of the International Searching Authority, mailed May 4, 2016.

Xin et al., "Electrochemical Behavior Al2O3/Al Coated Surgical Az91 Magnesium Alloy in Simulated Body Fluids," Journal of the Electrochemical Society, 155 (5) C178-C182 (2008).

Zhang et al., "Use of Graphene as Protection Film in Biological Environments" Scientific Reports, Feb. 14, 2014, pqs 1-8.

* cited by examiner

PROTECTED MAGNESIUM ALLOYS FOR BIORESORBABLE STENTS

CROSS-REFERENCE TO RELATED APPLICATIONS

This is a divisional application of U.S. patent application Ser. No. 16/442,740, filed Jun. 17, 2019, which is a divisional of U.S. patent application Ser. No. 14/934,645, filed Nov. 6, 2015, now U.S. Pat. No. 10,322,214, which claims the benefit of U.S. Provisional Application No. 62/076,214, filed Nov. 6, 2014.

FIELD

This disclosure generally relates to, among other things, implantable medical devices; and more particularly to implantable devices, such as stents, that include biodegradable magnesium alloys.

INTRODUCTION

Stents in general are prostheses or implants that can be inserted into a vessel or passageway of a patient and when deployed presses against the vessel or passageway. Stents are often endovascular prostheses or implants that are used for treating, for example, stenosis or aneurysms. Stents may include a support structure or frame that is capable of supporting a wall of a vessel or bypass an aneurysm. In many cases, the structural features of the stent consist of the frame.

Stents are typically inserted into a vessel in a compressed or crimped state and then expanded when properly positioned such that the frame presses against the wall of the vessel. The stents can be expanded with the aid of, for example, a balloon catheter or may be self-expandable.

Stents can be nondegradable or biodegradable. Nondegradable stents are designed to remain in the vessel for an unspecified period of time. Biodegradable stents are degraded over predetermined periods of time in the vessel. Preferably, a biodegradable stent begins to degrade when the vessel is healed and the support function of the stent is no longer needed.

Magnesium (Mg) alloys are currently being investigated as potential materials for, among other things, biodegradable stents. However, bare Mg alloys tend to degrade too quickly when implanted in a patient for the stents to effectively operate for a desired amount of time. Accordingly, it may be desirable to modify or protect Mg alloys of stents where an Mg alloy component would otherwise be exposed to bodily fluid or tissue so that the stents can effectively operate for the desired amount of time.

Developing effective Mg alloy modification or protection regimens can be challenging. For example, the modification or protection, such as a coating or surface treatment, should not only inhibit corrosion of the Mg alloy for a sufficient time after implant, but also should preferably be biodegradable and should preferably have suitable mechanical properties to inhibit cracking during implantation or use. In addition, it may also be desirable for the coating or surface treatment to serve as a good primer for a drug coating, which may be a polymer-containing or polymer-free coating.

SUMMARY

Described herein are a variety of modification or protection regimens for inhibiting corrosion or slowing biodegradation of Mg alloys. The modification or protection regimens include one or more of removing secondary phases, such as precipitants or defects, from a surface of the Mg alloy to provide more uniform corrosion across the surface rather than focused localized corrosion, and providing a temporary barrier to water to the surface of the Mg alloy. Removal of secondary phases can be accomplished in any suitable manner, such as conversion coating the Mg alloy surface. One particularly effective conversion coating is a hydrofluoric acid (HF) conversion coating. Providing a barrier to water to the Mg alloy surface can be accomplished in any suitable manner. For example, barrier layers may be deposited by atomic layer deposition (ALD), physical vapor deposition, or by drawing tubes of metal over the Mg alloy surface. The thickness of the deposited layers, the material of the layers and the process conditions of depositing the layers can be tuned to adjust the amount of time that the water barrier remains in place in vivo prior to, for example, biodegrading to an extent to no longer serve as an effective water barrier.

In some embodiments described herein, a biodegradable implantable medical device includes a magnesium (Mg) alloy and a coating on the Mg alloy. The coating comprises one or more of a conversion coating that at least partially removes surface secondary phases exposed on a surface of the Mg alloy, and one or more water barrier layers on or over the surface of the Mg alloy. In some embodiments, the Mg alloy surface is conversion coated with a hydrofluoric acid conversion coating; a conversion coating with acidic or basic solutions of $Ce^{3+}$ or $Ce^{4+}$; a conversion coating with acidic or basic solutions of inorganic Mg precipitating agents such as phosphates, silicates, permanganate, hydrotalcite ($Mg_6Al_2[OH]_{16}CO_3 \cdot 4H_2O$), vanadates, chromates and Rare Earth ionic solutions other than cerium; or a conversion coating with acidic or basic solutions of organic Mg precipitating agents such as 4-(4-nitrophenylazo)-resorcinol, 8-hydroxy quinoline and sodium dodecylbenzenesulphonate. In some embodiments, one or more barrier layer is deposited on an Mg alloy device surface or on a conversion coated Mg alloy device surface by ALD. In some embodiments, one or more of cerium oxide ($CeO_2$), aluminum oxide ($AlO_2$), titanium oxide ($TiO_2$) or metallo-organic variations such as ethylene and propylene glycols of titanium, zirconium oxide ($ZrO_2$) or metallo-organic variations of zirconium, hafnium oxide ($HfO_2$) or metallo-organic variations of hafnium, aluminum fluoride ($AlF_3$), and magnesium fluoride ($MgF_2$) are deposited by ALD. In some embodiments, the implantable medical device is a stent.

In some embodiments described herein, a biodegradable implantable medical device includes a magnesium (Mg) alloy and a coating on the Mg alloy. The coating includes a HF conversion coating layer on the Mg alloy and alternating layers of aluminum oxide ($Al_2O_3$) and a poly(aluminum ethylene glycol) polymer (alucone) on the HF conversion coating layer.

In some embodiments described herein, a method for manufacturing a biodegradable implantable medical device includes (i) forming a device comprising a magnesium (Mg) alloy, (ii) incubating the device with a composition comprising hydrofluoric acid (HF) to convert a surface of the Mg alloy to a hydrous magnesium fluoride ($MgF_2$) layer, (iii) depositing a layer or aluminum oxide ($Al_2O_3$) on the hydrous $MgF_2$ layer, and (iv) depositing a nanolaminate of $Al_2O_3$ and a poly(aluminum ethylene glycol) polymer (alucone) on the $Al_2O_3$ layer.

In some embodiments described herein, a biodegradable implantable medical device includes a magnesium (Mg)

alloy core and a first layer of magnesium over the core. The device may further comprise a layer of magnesium fluoride ($MgF_2$) between the Mg alloy core and the first layer of magnesium, on the first layer or magnesium, or between the Mg alloy core and the first layer of magnesium and on the first layer of magnesium. Alternatively, a layer of magnesium fluoride alone may be deposited on the surface of the Mg alloy.

In some embodiments described herein, a method for forming a biodegradable frame for an implantable medical stent includes (i) providing a tube having an inner layer of magnesium, an outer layer of magnesium, and a magnesium alloy layer between the inner and outer layers of magnesium; and (ii) laser cutting the tube to produce the frame.

In some embodiments described herein, a method for forming a biodegradable frame for an implantable medical stent includes (i) providing a wire comprising an inner layer of magnesium alloy and an outer layer of magnesium around the inner layer; and (ii) forming or welding the wire to produce the frame.

In some embodiments described herein, a biodegradable implantable medical device includes a magnesium (Mg) alloy and a coating on the Mg alloy. The coating comprises one or more water barrier layers. Non-limiting examples of water barrier layers include aluminum, magnesium, cerium oxide, aluminum oxide, titanium oxide or metallo-organic variations such as ethylene and prolylene glycols of titanium, zirconium oxide or metallo-organic variations of zirconium, hafnium oxide or metallo-organic variations of hafnium, aluminum fluoride, or magnesium fluoride. Other examples of water barriers include polymeric barriers. In some embodiments, the coating comprises a layer of aluminum oxide and a layer of cerium oxide.

In some embodiments described herein, a method for manufacturing and implantable medical device includes (i) providing a device comprising a magnesium (Mg) alloy, (ii) optionally incubating the frame with a composition comprising hydrofluoric acid (HF) to convert a surface of the Mg alloy to a hydrous magnesium fluoride ($MgF_2$) layer, (iii) depositing a water barrier layer on the Mg alloy or on the optional hydrous $MgF_2$ layer, if present. Non-limiting examples of water barrier layers include aluminum, magnesium, cerium oxide, aluminum oxide, titanium oxide or metallo-organic variations such as ethylene and prolylene glycols of titanium, zirconium oxide or metallo-organic variations of zirconium, hafnium oxide or metallo-organic variations of hafnium, aluminum fluoride, or magnesium fluoride. Other examples of water barriers include polymeric barriers. In some embodiments, the barrier layer comprises aluminum oxide. In some embodiments, depositing the water barrier layer on the Mg alloy or on the optional hydrous $MgF_2$ layer, if present, comprises depositing a layer of aluminum oxide and depositing a layer of cerium oxide. In some embodiments, a layer of cerium oxide is deposited on a layer of magnesium oxide.

In some embodiments described herein, a biodegradable implantable medical device includes a magnesium (Mg) alloy and a coating on the Mg alloy. The coating comprises a layer of aluminum and a layer of graphene.

In some embodiments described herein, a biodegradable implantable medical device includes (i) an Mg alloy core; (ii) a layer of $Mg_{17}Al_{12}$ on the core; (iii) a layer of aluminum on the layer of $Mg_{17}Al_{12}$; (iii) an optional aluminum oxide ($Al_2O_3$) layer on the layer of aluminum; and (iv) a layer of graphene on the layer of aluminum or the optional layer of $Al_2O_3$, if present.

In some embodiments described herein, a method for forming a biodegradable implantable medical device includes (i) providing a device comprising a magnesium (Mg) alloy; (ii) optionally incubating the device with a composition comprising hydrofluoric acid (HF) to convert a surface of the Mg alloy to a hydrous magnesium fluoride ($MgF_2$) layer; (iii) depositing a layer of aluminum on the Mg alloy or on the optional hydrous $MgF_2$ layer, if present, to produce an aluminum coated device; and (iv) depositing a layer of graphene on the aluminum coated device.

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, in which.

Figure 1:
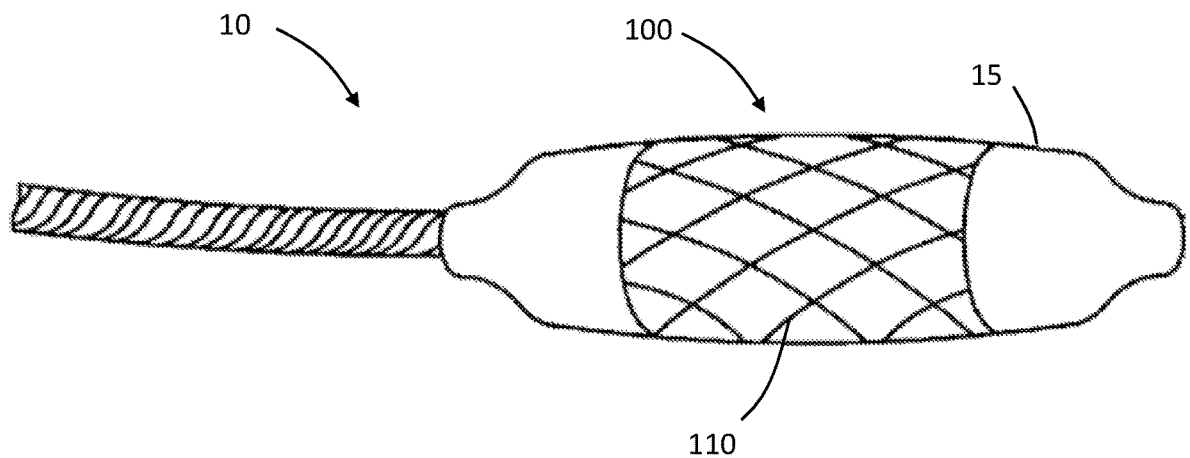
FIG. 1 is a schematic side view of an embodiment of stent and balloon catheter that can be used in accordance with some embodiments of the teachings presented herein.

The schematic drawings in are not necessarily to scale.

DETAILED DESCRIPTION

Reference will now be made in greater detail to various embodiments of the subject matter of the present disclosure, some embodiments of which are illustrated in the accompanying drawings. Like numbers used in the figures refer to like components, steps and the like. However, it will be understood that the use of a number to refer to a component in a given figure is not intended to limit the component in another figure labeled with the same number. In addition, the use of different numbers to refer to components in different figures is not intended to indicate that the different numbered components cannot be the same or similar to other numbered components.

Described herein are a variety of ways to protect Mg alloys to inhibit corrosion or slow biodegradation of the Mg alloys so that the Mg alloys perform, in vivo, for their intended purpose for a suitable amount of time. One way to protect Mg alloy devices from premature degradation following implantation is to modify an exposed surface of the implant so that the Mg alloy degrades more uniformly across its surface. Mg alloys typically have secondary phases, such as precipitants or defects, exposed on their surfaces, which exposed secondary phases result in focal points for corrosion. Focused local corrosion can result in premature failure of an implanted Mg alloy device. Modifying a surface of an Mg alloy device to at least partially remove exposed secondary phases can result in more uniform corrosion across the surface, and thus extend the life of the Mg alloy device. One way to modify a surface of an Mg alloy device to remove exposed surface secondary phases is to conversion coat the surface of the device. Examples of suitable conversion coating processes include hydrofluoric acid conversion coatings; conversion coating with acidic or basic solutions of $Ce^{3+}$ or $Ce^{4+}$; treatment with acidic or basic solutions of inorganic Mg precipitating agents such as phosphates, silicates, permanganate, hydrotalcite, vanadates, chromates and Rare Earth ionic solutions other than cerium; and conversion coating with acidic or basic solutions of organic Mg precipitating agents such as 4-(4-nitrophenylazo)-resorcinol, 8-hydroxy quinoline and sodium dodecylbenzenesulphonate.

Another way to protect Mg alloy devices from premature degradation following implantation is to provide a barrier to water to the Mg alloy surface of the device. Suitable water barriers can be deposited on the surface of an Mg alloy surface of the device or can be placed around or over an Mg alloy device. For example, a moisture barrier can be deposited on the surface of an Mg alloy by physical vapor deposition, ALD, or by drawing tubes or sheets over a surface of an Mg alloy device. Any suitable water barrier may be deposited on or placed over a surface of an Mg alloy device. Examples of suitable water barriers include aluminum, magnesium, cerium oxide, aluminum oxide, titanium oxide or metallo-organic variations such as ethylene and prolylene glycols of titanium, zirconium oxide or metallo-organic variations of zirconium, hafnium oxide or metallo-organic variations of hafnium, aluminum fluoride, or magnesium fluoride. Other examples of water barriers include polymeric barriers. Preferably, the barrier is biodegradable. The thickness of the barrier layers, the material of the barrier layers, and the process conditions by which the barrier layers are deposited on or disposed about the Mg alloy devices can be tuned to adjust the amount of time that the water barrier remains in place in vivo prior to, for example, biodegrading to an extent to no longer serve as an effective water barrier.

A conversion coating process, one or more coating process, or both a conversion coating process and one or more coating process can be employed to tailor the degradation rate of an Mg alloy device to delay biodegradation of an Mg alloy device for a desired amount of time.

The protection processes described herein can be used for any suitable medical device that contains an Mg alloy that would otherwise be exposed to bodily tissue or fluid when implanted in a patent. In various embodiments, the protected or modified Mg alloys are employed in, or as, frames for medical stents.

In some embodiments, the stents are endovascular stents for treating, for example, stenosis or aneurysms. The stents may comprise, consist essentially of, or consist of a frame that is capable of supporting a wall of a vessel or bypass an aneurysm. The stents are typically inserted into a vessel in a compressed or crimped state and then expanded when properly positioned such that the frame presses against the wall of the vessel. In many embodiments, a balloon catheter is used to insert the stent into the vessel. The crimped stent is disposed over the balloon of the catheter. Once in a proper position within the vessel, the balloon is inflated to expand the stent. The balloon can be deflated, and the catheter can be removed from the vessel leaving the expanded stent in place within the vessel.

Referring now to FIG. 1, a schematic illustration of a stent 100 having a frame 110 is shown disposed over a balloon 15 of a balloon catheter 10. The depicted balloon 15 is inflated and the stent 100 is thus expanded. The frame 110 of the stent 100 can be formed from a modified or protected Mg alloy as described herein.

Preferably, the modifications or protections described herein prevent biodegradation of the Mg alloy to an extent that allows the sent to effectively support the vessel until the vessel is healed and the support function of the stent is no longer needed. The length of time needed until the vessel is healed can vary depending on the patient, the severity of the disease, and the like. In many cases, the length of time needed until the vessel is healed will be in a range from about one year to about two and a half years.

Ideally no biodegradation of the stent would occur until the vessel is healed, and once the vessel is healed biodegradation would occur rapidly. Practically, however, biodegradation over time will likely deviate from the ideal path. It should be sufficient for the protections described herein to prevent a biodegradation of an Mg alloy to an extent that allows the stent to function properly until the vessel is healed. One or more of the processes or sub-processes for protecting Mg alloys can be combined or tailored to achieve an appropriate biodegradation profile.

A frame of a stent can include any suitable magnesium alloy. Examples of suitable magnesium alloys include commercially available Mg alloys such as AZ series (Mg—Al—Zn), AM series (Mg—Al—Mn), AE series (Mg—Al-RE), EZ series (Mg-RE-Zn), ZK series (Mg—Zn—Zr), WE series (Mg-RE-Zr), AX or AXJ series (Mg—Al—Ca), and AJ series, wherein RE indicates a rare earth metal. In some embodiments, a frame of a stent can includes a rare earth doped Mg alloys, such as an AE or WE series Mg alloy, which have very good mechanical properties such as high yield strength and elongation.

1. Overview of Mg Alloy Protection Processes

Described herein are a variety of ways to protect Mg alloys to inhibit corrosion or slow biodegradation of the Mg alloys. An overview of some of the ways to inhibit corrosion and thus slow biodegradation of Mg alloys is first presented below, followed with a more detailed description of selected embodiments for protecting Mg alloys.

One way to protect Mg alloys to inhibit corrosion or to slow biodegradation is to treat the Mg alloy to make corrosion more uniform across the Mg alloy surface. Uniform corrosion spread out over the surface of the Mg alloy may be an important factor in improving the functional effectiveness, such as the structural integrity, of a biodegradable stent over time. Non-uniform, localized corrosion, which tends to focus at, for example exposed surface precipitants or defects, may result in more rapid failure of a stent frame due to localized weakness. One particularly effective way to inhibit non-uniform localized corrosion is to conversion coat the Mg alloy via a process that results in partial or complete removal of exposed metallic precipitants and defects on the Mg alloy surface to provide for more uniform corrosion. Examples of conversion coatings that may remove exposed precipitants or defects from a surface of an Mg alloy include, but are not limited to, hydrofluoric acid conversion coatings; conversion coatings with acidic or basic solutions of $Ce^{3+}$ or $Ce^{4+}$; conversion coatings with acidic or basic solutions of inorganic Mg precipitating agents such as phosphates, silicates, permanganate, hydrotalcite, vanadates, chromates and Rare Earth ionic solutions other than cerium; and conversion coating with acidic or basic solutions of organic Mg precipitating agents such as 4-(4-nitrophenylazo)-resorcinol, 8-hydroxy quinoline and sodium dodecylbenzenesulphonate. One particularly effective conversion coating is an HF conversion coating.

While HF conversion coating provides for more uniform corrosion, it may not, by itself, sufficiently slow degradation of an Mg alloy stent frame to allow the stent to function effectively for a desired amount of time. Accordingly, an additional protective layer may be placed on the HF conversion coated Mg alloy stent frame to delay the onset of corrosion. Any one or more suitable protective layers that serve as a water barrier may be used. Examples of suitable protective layers include, but are not limited to, aluminum, magnesium, cerium oxide, aluminum oxide, titanium oxide or metallo-organic variations such as ethylene and propylene glycols of titanium, zirconium oxide or metallo-organic variations of zirconium, hafnium oxide or metallo-organic variations of hafnium, aluminum fluoride, or magnesium fluoride. The thickness of the barrier layers, the material of the barrier layers, and the process conditions by which the barrier layers are deposited on or disposed about the Mg alloy stent frame can be tuned to adjust the amount of time that the water barrier remains in place in vivo prior to, for example, biodegrading to an extent to no longer serve as an effective water barrier and allow more rapid biodegradation of the Mg alloy stent frame. In some examples, one or more additional protective layers may include magnesium, aluminum oxide, cerium oxide, polymers and graphene. One particularly effective additional coating comprises alternating layers of aluminum oxide and a poly(aluminum ethylene glycol) polymer (alucone).

Another way to protect Mg alloys to inhibit corrosion or to slow biodegradation is to deposit a metallic layer on the Mg alloy under conditions to form an intermetallic layer that is more resistant to corrosion than the Mg alloy. One example of an effective way to inhibit corrosion is to deposit aluminum on the Mg alloy and then heat treat the aluminum-coated Mg alloy to form an Mg/Al intermetallic layer. A commonly formed intermetallic compound is corrosion resistant $Mg_{17}Al_{12}$.

While aluminum coating and heat treatment can inhibit corrosion of an Mg alloy, it may not, by itself, sufficiently slow degradation of an Mg alloy stent frame to allow the stent to function effectively for a desired amount of time. Accordingly, an additional protective layer may be placed on the aluminum coated Mg alloy stent frame to delay onset of corrosion. Any one or more suitable protective layers that serve as a water barrier may be used. Examples of suitable protective layers include, but are not limited to, aluminum, magnesium, cerium oxide, aluminum oxide, titanium oxide or metallo-organic variations such as ethylene and propylene glycols of titanium, zirconium oxide or metallo-organic variations of zirconium, hafnium oxide or metallo-organic variations of hafnium, aluminum fluoride, or magnesium fluoride. The thickness of the barrier layers, the material of the barrier layers, and the process conditions by which the barrier layers are deposited on or disposed about the Mg alloy stent frame can be tuned to adjust the amount of time that the water barrier remains in place in vivo prior to, for example, biodegrading to an extent to no longer serve as an effective water barrier and allow more rapid biodegradation of the Mg alloy stent frame. In some examples, one or more additional protective layers include one or more layer of magnesium, aluminum oxide, cerium oxide, polymers and graphene. One particularly effective additional coating comprises graphene, which provides corrosion resistance and has good elongation properties.

Another way to protect Mg alloys to inhibit corrosion or to slow biodegradation is to deposit a water barrier layer on the Mg alloy or disposed a water barrier about the Mg alloy. Suitable water barriers may include one or layers of aluminum, magnesium, cerium oxide, aluminum oxide, titanium oxide or metallo-organic variations such as ethylene and propylene glycols of titanium, zirconium oxide or metallo-organic variations of zirconium, hafnium oxide or metallo-organic variations of hafnium, aluminum fluoride, or magnesium fluoride. The thickness of the barrier layers, the material of the barrier layers, and the process conditions by which the barrier layers are deposited on or disposed about the Mg alloy stent frame can be tuned to adjust the amount of time that the water barrier remains in place in vivo prior to, for example, biodegrading to an extent to no longer serve as an effective water barrier and allow more rapid biodegradation of the Mg alloy stent frame.

One example of a suitable barrier includes alternating layers of aluminum oxide and cerium oxide. Aluminum oxide provides good corrosion resistance to Mg alloys. However, when subjected to stress, such as occurs during crimping or deployment of a stent frame or during in vivo fatigue of the stent frame, the aluminum oxide coating can crack and become less effective. Cerium can also act as a corrosion inhibitor for Mg alloys and, unlike aluminum oxide, may have self-healing properties such as the ability to fill cracks due to fatigue or corrosion. However, coating Mg alloys with cerium may present challenges. For example, cerium nitrate conversion coatings are flaky and do not adhere well to the surface of Mg alloy. By way of further example, atomic layer deposition (ALD) of cerium oxide is typically performed at high temperatures that may cause vaporization of the Mg alloy during the ALD process. As described herein, an Mg alloy may be coated with aluminum oxide, for example by ALD at sufficiently low temperatures to not cause appreciable Mg alloy vaporization, and then the aluminum oxide-coated Mg alloy may be coated with cerium oxide, for example by ALD because the aluminum-oxide will prevent Mg alloy vaporization.

Prior to coating aluminum oxide and cerium oxide on the Mg alloy, the Mg alloy may be HF conversion coated or coated with aluminum and heat treated.

Another way to protect Mg alloys to inhibit corrosion or to slow biodegradation is to place a layer of magnesium over or about the Mg alloy. Magnesium has a slower degradation rate than Mg alloys, but has poor mechanical properties, such as low yield strength and low elongation, for use as stent frames. In contrast, Mg alloys have higher strength but poor corrosion resistance due to the presence of second phases at grain boundaries that may lead to intergranular corrosion and subsequent failure of Mg alloy stent frames in corrosive environments. By providing a layer of magnesium over or around an Mg alloy layer, a combination of the desired mechanical properties of the Mg alloy and the corrosion resistance of the magnesium results.

One effective way to provide a layer of magnesium over an Mg alloy is to draw a magnesium tube over an Mg alloy tube. The Mg alloy tube may also be drawn over an inner magnesium tube to provide a tri-layer tube that can be made into a stent frame by, for example, laser cutting.

Another effective way to provide a layer of magnesium around an Mg alloy is to draw a magnesium tube over an Mg alloy wire to form a bi-layer wire that can be, for example, formed and welded into a stent frame.

Prior to placing a magnesium layer over or around the Mg alloy, the Mg alloy tube or wire may be coated or treated as described above. For example, the Mg alloy tube or wire can be HF conversion coated, coated with aluminum and heat treated, coated with alternating layers of aluminum oxide and cerium oxide, coated with a polymer or graphene, or the like.

Overviews of the various ways discussed above to protect Mg alloys to inhibit corrosion or to slow biodegradation are presented in FIGS. 2-5. Referring now to the method of FIG. 2, an Mg alloy stent frame or a precursor to a stent frame, such as a tube that may be laser cut into a stent frame or a wire that may be formed and welded into a stent frame, may be HF conversion coated (200). An additional coating may be applied to the HF conversion coated Mg alloy frame or frame precursor (210). The additional coating may include, for example, alternating layers of aluminum oxide and alucone.

Figure 3:
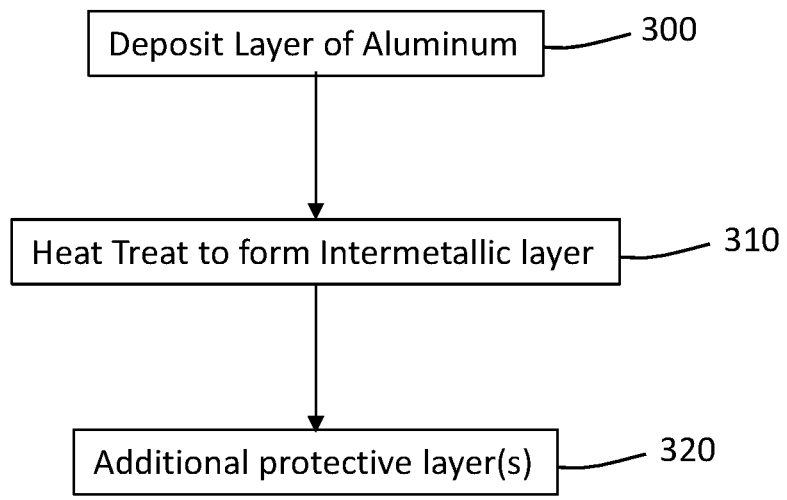

Referring now to another method shown in FIG. 3, a layer of aluminum may be deposited on an Mg alloy stent frame or stent frame precursor (300), and the resulting aluminum coated Mg alloy frame or frame precursor may be heat treated (310). Heat treatment may form an Mg/Al intermetallic layer, such as $Mg_{17}Al_{12}$. An additional coating may be applied to the heat treated, aluminum coated Mg alloy frame or frame precursor (320). The additional coating may include, for example, graphene.

Figure 4:
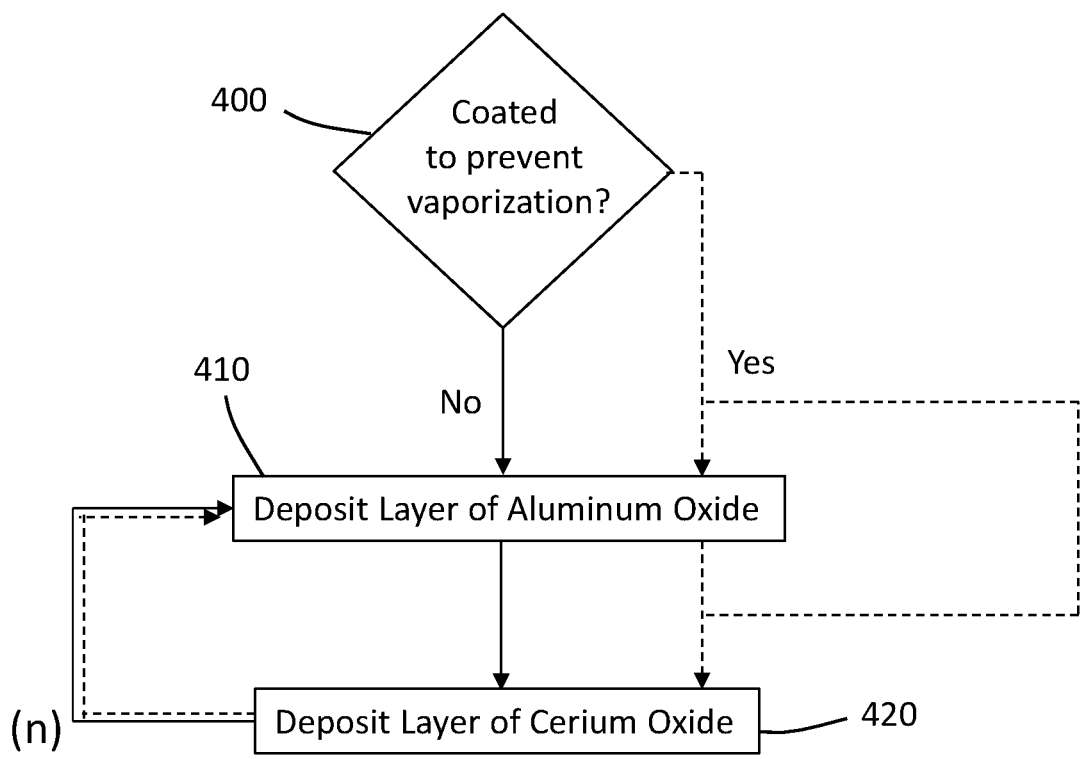

Referring now to another method shown in FIG. 4, Alternating layers of aluminum oxide and cerium oxide may be deposited on a frame or frame precursor (410, 420). If the Mg alloy frame or frame precursor is not optionally coated to prevent Mg alloy vaporization at process conditions for cerium oxide deposition (400), the frame or frame precursor is preferably first coated with a layer of aluminum oxide (410) prior to depositing cerium oxide (420). Aluminum deposition and heat treatment (e.g., as discussed above regarding FIG. 3) is an example of a coating that may prevent Mg alloy vaporization under cerium oxide deposition conditions. If the Mg alloy frame or frame precursor is coated to prevent Mg alloy vaporization (400), either (i) a layer of cerium oxide may be deposited (420) prior to depositing a layer of aluminum oxide (410), or (ii) a layer of aluminum oxide may be deposited (410) prior to depositing a layer of cerium oxide (420). Any suitable number (n) of alternating layers of aluminum oxide and cerium oxide may be deposited. For example, from 1 to 500 layers of aluminum oxide may be deposited (410) and from 1 to 500 layers of cerium oxide may be deposited (420).

Figure 2:
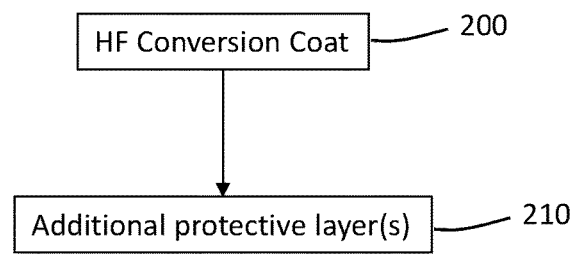
FIGS. 2-5 are schematic flow diagrams of embodiments of methods for protecting Mg alloy stent frames to inhibit corrosion and thus to slow biodegradation.
Figure 5:
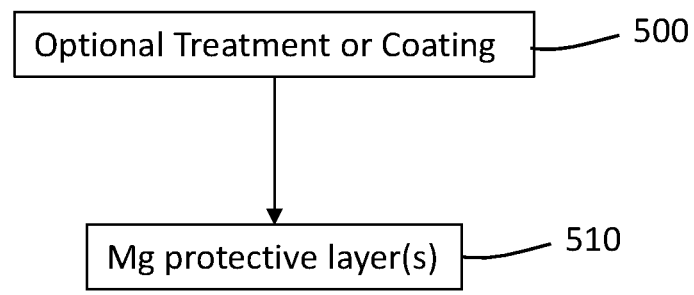

Referring now to another method shown in FIG. 5, an Mg alloy stent frame or frame precursor may optionally be treated or coated (500); e.g., in any one of the above described examples of FIGS. 2-4. Thus, in addition to one of the methods of FIGS. 2-4, a protective layer of magnesium may be placed over or around the optionally treated or coated Mg alloy frame or frame precursor (510). For example, a magnesium tube may be drawn over an optionally treated or coated Mg alloy wire. Alternatively, (i) an optionally treated or coated Mg alloy tube may be drawn over a magnesium tube; (ii) a magnesium tube may be drawn over the optionally treated or coated Mg alloy tube; or (iii) the optionally treated or coated Mg alloy tube may be drawn over a magnesium tube and a magnesium tube may be drawn over the optionally treated or coated Mg alloy tube. If the Mg alloy tube is not treated or coated, preferably the Mg alloy tube is drawn over a magnesium tube and a magnesium tube drawn over the Mg alloy tube.

Brief overview of methods for protecting Mg alloy stent frames have been discussed above. Additional details regarding some embodiments of the processes and resulting frames or frame precursors are presented below.

2. HF Conversion Coating and Additional Layer

As discussed above, an Mg alloy stent frame or stent frame precursor may advantageously be HF conversion coated to render corrosion of the frame more uniform, which can delay frame failure relative non-HF conversion coated frames that are susceptible to enhanced localized corrosion. However, it may be desirable to deposit an additional corrosion-resistant layer on the HF conversion coated Mg alloy stent frame to slow the rate of corrosion of the Mg alloy stent frame or stent frame precursor.

Accordingly and in some embodiments described herein, an Mg alloy frame or a precursor to a frame, such as a tube that can be laser cut into a frame or wire that can be formed or welded into a frame, is treated with hydrofluoric acid (HF) to form a HF conversion coating layer on the Mg alloy. HF conversion coatings on Mg alloys form a magnesium fluoride ($MgF_2$) layer, which alone may not sufficiently slow corrosion of the Mg alloy.

Advantageously, HF conversion coating treatments of Mg alloys result in removal of precipitants and defects on the Mg alloy surface. Precipitants and defects may cause enhanced localized corrosion on surfaces stent frames formed from Mg alloys. Enhanced localized corrosion leads to localized weaknesses in the frame and premature mechanical failure of the frame at the localized weaknesses. By removing precipitants and defects that may cause enhanced local corrosion, HF conversion coating of Mg alloy stent frames results in more uniform corrosion of the stent frames, and thus more even degradation of the frames (as opposed to enhanced localized corrosion leading to localized failure). Uniform corrosion, which is spread out across the surface of the Mg alloy stent frame, may thus be an important factor in improving the functional effectiveness, such as the structural integrity, of a biodegradable stent over time.

An Mg alloy frame or frame precursor, which will both be referred to hereinafter as a "frame," can be HF conversion coated in any suitable manner. Typically, an Mg alloy frame is treated with hydrofluoric acid at a suitable concentration for a suitable amount of time and under suitable conditions to form a layer of $MgF_2$ on a surface of the frame. By way of example, an Mg alloy frame can be immersed in a 49% HF solution for 24 hours at ambient conditions to form an HF conversion coating. The resulting coated frame tends to be uniform and dark in appearance.

Because the resulting HF conversion coating may not sufficiently slow corrosion, another coating or treatment may be applied.

In some embodiments, a layer of aluminum or aluminum oxide ($Al_2O_3$) is deposited on the HF conversion coated Mg alloy frame. If aluminum is deposited, the resulting aluminum coated frame can be heated in the presence of oxygen to produce an outer surface of aluminum oxide. Preferably, the aluminum or aluminum oxide is initially deposited at a temperature of 150° C. or less, such as 100° C. or less or 95° C. or less. Temperatures above 150° C. may result in vaporization of the Mg alloy under vacuum, which is typically applied in deposition processes.

Because aluminum applied at such low temperatures tends to be amorphous, the resulting aluminum coated frame can be heated at a suitable temperature for a sufficient time to convert the amorphous film to a crystalline film. Once applied, the amorphous film should prevent vaporization of the underlying Mg alloy. By way of example, an aluminum coated stent can be heated at temperatures greater than 350° C., such as greater than 400° C. or about 450° C. A few minutes to about an hour should be sufficient to convert amorphous aluminum to crystalline aluminum. As indicated above, heating in the presence of oxygen or an oxidizer can produce an outer layer of aluminum oxide.

Any suitable deposition process can be employed to deposit a layer of aluminum or aluminum oxide. For example, physical vapor deposition or atomic layer deposition may be employed. Aluminum oxide is preferably deposited by atomic layer deposition (ALD), which may occur at temperatures of, for example, about 75° C. to about 95° C.

While aluminum oxide films, such as ALD aluminum oxide films, can slow corrosion and thus slow the biodegradation of Mg alloy frames. ALD aluminum oxide films can be brittle and may crack upon crimping or deployment of the stent or may crack while undergoing fatigue after implantation, particularly at high stress areas. If the film is cracked, its ability to protect the Mg alloy substrate may be compromised.

In some embodiments, an additional layer is applied to an aluminum or aluminum oxide coated Mg alloy frame. Any suitable additional layer may be applied. In some embodiments, an additional layer contains cerium oxide ($CeO_2$). For example, alternating layers of cerium oxide and aluminum oxide may be applied. In some embodiments, an additional layer contains graphene. In some embodiments, an additional layer is a magnesium layer. In some embodiments, an additional layer contains an organic component.

In some embodiments a layer including an organic component contains a poly(aluminum ethylene glycol) polymer (alucone). Such layers can be applied in any suitable manner such as, for example, molecular layer deposition (MLD) at any suitable temperature, such as about 120° C. to about 130° C. In some embodiments, layers of aluminum oxide and alucone are alternated to form a nanolaminate. In some embodiments, a cap layer of alucone is deposited. The aluminum oxide layers and alucone layers, in combination, can have any suitable thickness, whether or not in the form of a nanolaminate. In some embodiments, the combined thickness of the aluminum oxide layers and alucone layers is 100 nanometers (nm) or less.

A layer including an organic component can improve flexibility relative to the inorganic ALD films, but may have reduced barrier properties to moisture. However a layer including an organic component together with a metal or metal oxide layer, such as an aluminum oxide layer, may form an effective barrier. As discussed below in the EXAMPLES, Mg alloy frames coated with aluminum oxide and alucone nanolaminates had superior barrier and flexibility properties relative to either coating alone. When such nanolaminates were coated on bare Mg alloy, as opposed to HF conversion coated Mg alloy, the frame suffered from local corrosion issues. However, when used in combination with the HF conversion coating, the aluminum oxide/alucone nanolaminate resulted in slow and uniform corrosion that was not achieved with either HF conversion coating alone or nanolaminate coating alone.

As discussed above, the HF conversion coating provides for uniform corrosion of the base metal. The HF conversion coating may also improve adhesion of the aluminum oxide/alucone nanolaminate film. The aluminum oxide/alucone nanolaminate film provides a combination of flexibility and barrier properties to resist fracturing during the crimp and deploy process to effectively keep water and electrolytes away from the magnesium surface.

The combination of HF conversion coating and aluminum oxide/alucone nanolaminate coating provides an effective corrosion resistant barrier on Mg alloy substrates to delay biodegradation of Mg alloy-based stent frames. As discussed in the Examples below, the corrosion resistance provided by HF conversion coating alone and an aluminum oxide/alucone nanolaminate alone (without HF conversion coating) was substantially less effective at inhibiting corrosion of Mg alloy substrates than a combination of HF conversion coating and aluminum oxide/alucone nanolaminate coating. The unique combination of the uniform corrosion provided by the HF conversion coating with the flexibility and barrier properties of the aluminum oxide/alucone film results in slow and uniform corrosion across the stent surface and results in a stent that maintains high strength and radial stiffness.

Figure 6:
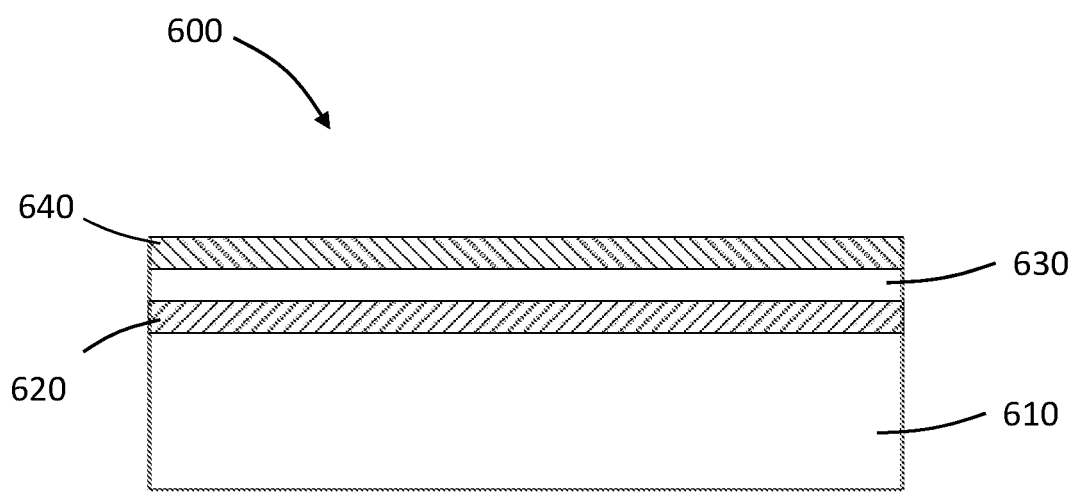
FIGS. 6-8 are schematic sectional views of embodiments of portions of stent frames.

For purposes of illustration, a schematic sectional view of an embodiment of a coated surface of an Mg alloy frame 600 is depicted in FIG. 6. The frame 600 includes an Mg alloy 610 and an $MgF_2$ layer 620 on the Mg alloy 610 resulting from HF conversion coating. A layer of aluminum oxide 630 is deposited on the $MgF_2$ layer 620, e.g., by ALD. A layer of alucone 640 is deposited; e.g. by MLD, on the layer of aluminum oxide 630. While only one layer of aluminum oxide 630 and one layer of alucone 640 are shown, it will be understood that the frame 600 may include multiple alternating layers of aluminum oxide and alucone, such as a nanolaminate of aluminum oxide and alucone. It will be understood that all surfaces of the Mg alloy 610, rather than the one surface depicted in FIG. 6, may be coated.

3. Deposition of Aluminum, Heat Treatment, and Additional Layer

As discussed above, an Mg alloy stent frame may advantageously be coated with aluminum and heat treated to produce a corrosion resistant intermetallic layer. A commonly formed intermetallic compound is corrosion resistant $Mg_{17}Al_{12}$.

Preferably, the aluminum is initially deposited at a temperature of 150° C. of less, such as 100° C. or less or 95° C. or less. Temperatures above 150° C. may result in vaporization of the Mg alloy under vacuum, which is typically applied in deposition processes. Because aluminum applied at such low temperatures tends to be amorphous and nanoporous, the resulting aluminum coated frame can be heated at a suitable temperature for a sufficient time to convert the amorphous film to a denser less porous polycrystalline aluminum film. Once applied, the amorphous film should prevent vaporization of the underlying Mg alloy. By way of example, an aluminum coated stent can be heated at temperatures greater than 350° C., such as greater than 400° C. or about 450° C. A few minutes to about an hour should be sufficient to convert amorphous aluminum to the denser polycrystalline aluminum. Heating in the presence of oxygen or an oxidizer can produce an outer layer of aluminum oxide.

Any suitable deposition process can be employed to deposit a layer of aluminum. For example, physical vapor deposition may be employed.

While aluminum coating and heat treatment can inhibit corrosion of an Mg alloy, it may not, by itself, sufficiently slow degradation of an Mg alloy stent frame to allow the stent to function effectively for a desired amount of time. Accordingly, one or more additional protective layer may be placed on the aluminum coated Mg alloy stent frame to further inhibit corrosion. Suitable additional protective layers include, for example, one or more layers of magnesium, cerium oxide, aluminum oxide, polymers and graphene.

In some embodiments, an Mg alloy is coated according to the following process:
1. Mg alloy surface is sand or grit blasted to create a textured surface. The sand or grit blasting can be done with $SiO_2$ or $Al_2O_3$ particles. For stent application the grit size should be smaller than 20 microns to avoid mechanical damage to the component. In addition, the air pressure should be minimal in order to minimize mechanical damage to the component.
2. The second step involves coating aluminum on to the textured Mg alloy surface by physical vapor deposition (PVD) process. The temperature of the stent component is preferably contained within or below 150° C. to avoid vaporization of the Mg alloy based material in vacuum.
3. The aluminum sputtered film can be made porous or fully dense by controlling the process parameters during the sputtering process. The films are generally amorphous in nature due to low temperature of the deposition process.
4. The third step involves, heat treating the aluminum sputtered Mg alloy based substrates at high temperatures, such as 450° C. for a few minutes to an hour in an argon environment to change the amorphous film to crystalline. In this process, some diffusion at the interface between the aluminum sputtered film and Mg alloy to form an MgAl intermetallic compound. The most commonly formed intermetallic compound is $Mg_{17}Al_{12}$. If the heat treatment process is carried in air or oxygen, thin oxide film will form on a surface of the aluminum. The film can be porous or dense depending upon the base sputtered aluminum layer.
5. The fourth step involves, depositing either a graphene or polymeric coating on to the heat treated surface of sputtered aluminum. The surface texture of the heat treated sputtered aluminum film helps to better adhere the graphene or polymeric coating to protect the surface from corrosion.

Graphene can be applied in any suitable manner, such as by spray coating, and may be coated one atomic layer thick.

Figure 7:
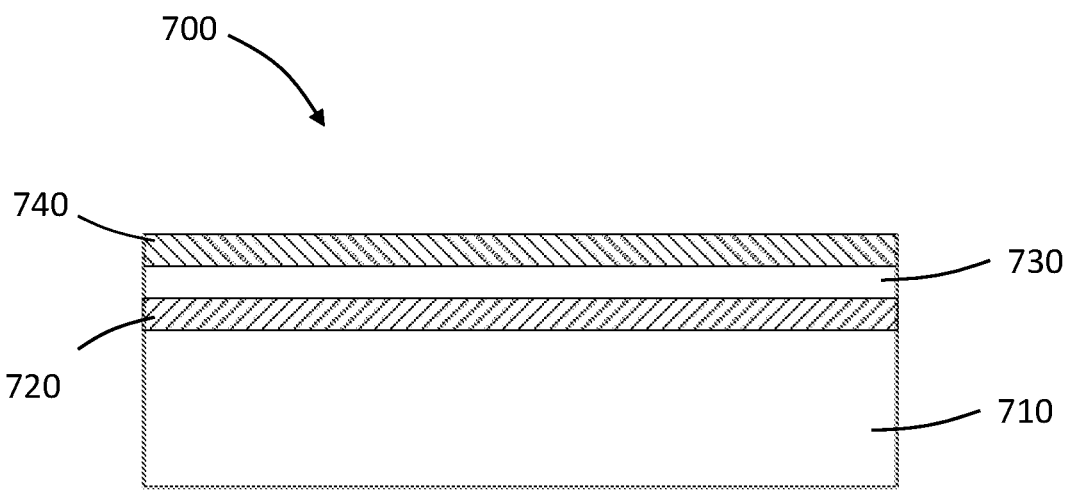

Referring now to FIG. 7, a schematic sectional view of a coated surface of an Mg alloy frame 700 according an embodiment described above is depicted. The frame 700 includes an Mg alloy 710, an intermetallic interface 720 formed by the Mg alloy 710 and deposited sputtered aluminum 730. A layer of graphene 740, which can be one atomic layer thick, is deposited on the layer of aluminum 730. The layer of aluminum 730 can have an upper surface of aluminum oxide, depending on the process conditions as discussed above. The layer of aluminum 730 can be porous or non-porous, depending on the process conditions as discussed above. It will be understood that all surfaces of the Mg alloy 710, rather than the one surface depicted in FIG. 7, may be coated.

4. Deposition of Aluminum Oxide and Cerium Oxide

As discussed above, an Mg alloy stent frame may advantageously be coated with one or more alternating layers of aluminum oxide and cerium oxide. Aluminum oxide provides good corrosion resistance to Mg alloys, but tends to crack when subjected to stress, which occurs during crimping or deployment of a stent frame or during in vivo fatigue of the stent frame. Cerium oxide can also act as a corrosion inhibitor for Mg alloys and, unlike aluminum oxide, may have self-healing properties. However, coating Mg alloys with cerium has presented challenges. For example, cerium nitrate conversion coatings are flaky and do not adhere well to the surface of Mg alloy. By way of further example, atomic layer deposition (ALD) of cerium oxide is typically performed at high temperatures that may cause vaporization of the Mg alloy during the ALD process.

As described herein, an Mg alloy stent frame may be coated with aluminum oxide, for example by ALD at sufficiently low temperatures to avoid appreciable Mg alloy vaporization, and then the aluminum oxide-coated Mg alloy may be coated with cerium oxide, for example by ALD, because the aluminum-oxide will prevent Mg alloy vaporization. The combination of the corrosion resistant properties and low temperature deposition process of aluminum oxide and the corrosion resistant and self-healing properties of cerium oxide can provide an effective corrosion resistant coating to Mg alloy stent frames to delay biodegradation of the frames.

Prior to coating aluminum oxide and cerium oxide on the Mg alloy, the Mg alloy may be HF conversion coated or coated with aluminum and heat treated; e.g., as described above. Alternatively, the Mg alloy may be coated with any other suitable material or materials prior to coating with aluminum oxide and cerium oxide.

In some embodiments, an Mg alloy frame is coated with aluminum oxide prior to coating with cerium oxide. As discussed above, aluminum oxide ALD can occur at temperatures less than 150° C., such as less than 100° C., and once deposited should prevent Mg vaporization at higher temperatures. Accordingly, cerium oxide may be deposited an aluminum oxide coated Mg alloy frame by, for example, ALD at temperatures of about 300° C. without concern for Mg alloy vaporization.

In some embodiments, alternating layers of aluminum oxide and cerium oxide are deposited on an Mg alloy or on a coating that is on an Mg alloy. Each layer of aluminum oxide and cerium oxide can have any suitable thickness, such as about 5 nm or more, 20 nm or more, or about 50 nm. In some embodiments, one or more layers of aluminum oxide and cerium oxide have a thickness of 10 nm or less, such as from about 3 nm to about 7 nm, or about 5 nm. In some embodiments, one or more layer of aluminum oxide and cerium oxide has a thickness in a range from about 5 nm to about 60 nm. Typically, the total combined thickness of the aluminum oxide layers and the cerium oxide layers will be 100 nm or less. In some embodiments, the coatings are applied stepwise to have either 50 nm of $Al_2O_3$ followed by 50 nm of $CeO_2$ or in the reverse order. A three-layer coating of $Al_2O_3$—$CeO_2$—$Al_2O_3$ is another embodiment contemplated herein.

Figure 8:
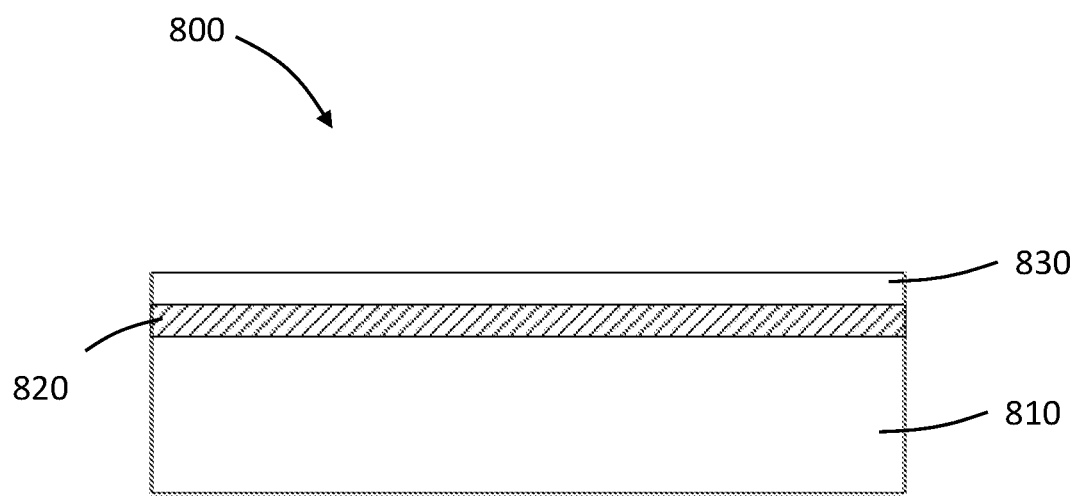

For purposes of illustration, a schematic sectional view of an embodiment of a coated surface of an Mg alloy frame 800 is depicted in FIG. 8. The frame 800 includes an Mg alloy 810 and an aluminum oxide layer 820 deposited on the Mg alloy 810 by, for example, ALD. A layer of cerium oxide 830 is deposited on the aluminum oxide layer 820, e.g., by ALD. While only one layer of aluminum oxide 820 and one layer of alucone 830 are shown, it will be understood that the frame 800 may include multiple alternating layers of aluminum oxide and alucone, such as a nanolaminate of aluminum oxide and alucone. It will be understood that all surfaces of the Mg alloy 810, rather than the one surface depicted in FIG. 8, may be coated.

5. Protective Layer or Layers of Magnesium

As discussed above, one or more protective layers of magnesium may be advantageously placed over or about an Mg alloy stent frame. Magnesium has a slower degradation rate than Mg alloys, but has mechanical properties that are not particularly suitable for use in stent frames. In contrast, Mg alloys have more suitably mechanical properties but tend to corrode more quickly than magnesium. As discussed above AE or WE series Mg alloys, which are rare earth metal doped Mg alloys, have particularly good mechanical properties for use as stent frames. However, the presence of second phases at grain boundaries leads to intergranular corrosion and subsequent failure of stent frames in corrosive environments. By providing a layer of magnesium over or around an Mg alloy, such as an AE or WE Mg alloy, a combination of the desired mechanical properties of the Mg alloy and the corrosion resistance of the magnesium results.

Prior to placing a magnesium layer over or around the Mg alloy, the Mg alloy may be coated or treated as described herein. For example, the Mg alloy may be HF conversion coated, coated with aluminum and heat treated, coated with alternating layers of aluminum oxide and cerium oxide, coated with a polymer or graphene, or the like.

As used herein "magnesium" and "pure magnesium" are used interchangeably. For purposes of the present disclosure, "pure" magnesium means magnesium that contains less than 50 parts per million (ppm) of another metal, preferably less than 10 ppm. In particular, "pure" magnesium preferably contains less than 10 ppm iron, copper and nickel. One effective way to provide a layer of magnesium over an Mg alloy is to draw a magnesium tube over an Mg alloy tube. In addition or alternatively, the Mg alloy tube may be drawn over an inner magnesium tube. The resulting bi- or a tri-layer tube can be made into a stent frame by, for example, laser cutting. Preferably, the resulting tube comprises an Mg alloy core between inner and outer layers of magnesium, if the Mg alloy tube is not corrosion resistant treated or coated; e.g., HF conversion coated, coated with aluminum and heat treated, coated with alternating layers of aluminum oxide and cerium oxide, coated with a polymer or graphene, or the like.

In some embodiments a tri-layer tube is formed by drawing an Mg alloy tube over an Mg tube to form a pre-tube having an inner layer of Mg. Another Mg tube may be over the pre-tube to form the tri-layer tube having an inner layer of Mg, an outer layer of Mg, and an Mg alloy layer between the inner and outer layers of magnesium. A stent frame can be laser cut from the tube or formed in any other suitable manner.

Figure 9:
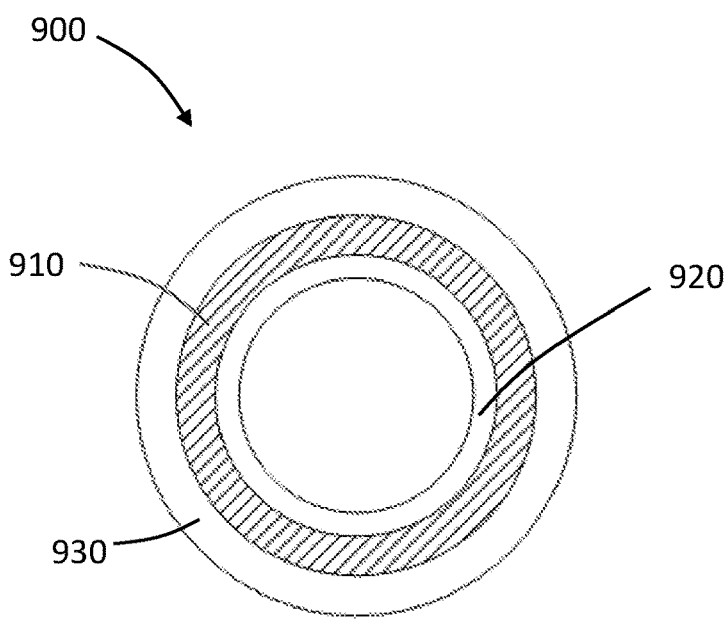
FIG. 9 is a schematic sectional view of an embodiment of a tube for forming a stent frame.

For purposes of illustration, a sectional view of an embodiment of a tube 900 from which a stent frame can be formed is shown in FIG. 9. The tube 900, and thus the resulting frame, includes an inner Mg layer 920, an outer Mg layer 930, and a layer of Mg alloy 910 between the inner and outer layers.

An effective way to provide a layer of magnesium around an Mg alloy is to draw a magnesium tube over an Mg alloy wire to form a bi-layer wire that can be, for example, formed and welded into a stent frame.

Figure 10:
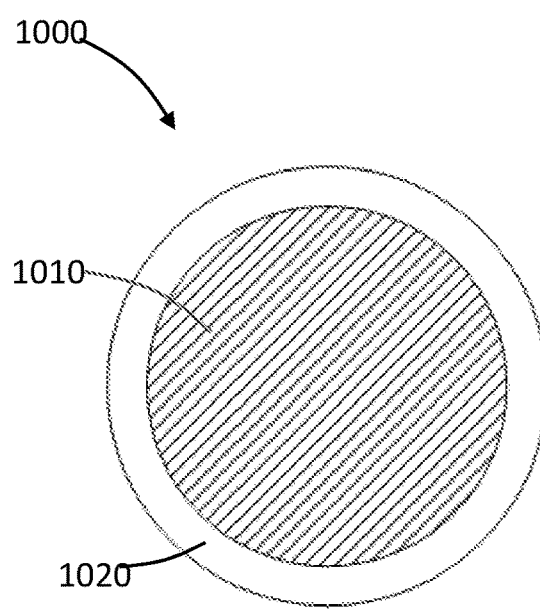
FIG. 10 is a schematic sectional view of an embodiment of a wire for forming a stent frame.

For purposes of illustration, a sectional view of an embodiment of a wire 1000 that may be used to form a stent frame is shown in FIG. 10. The wire 1000, and thus the resulting frame, includes an Mg alloy core 1010 and an Mg layer 1020 over the core 1010.

6. Combination of Protective Layers and Treatments

It will be understood that any suitable combination of coating, treatment or covering described herein can be employed. For example, an HF conversion coating as depicted in and discussed regarding FIG. 6 may be applied to an Mg alloy depicted in and discussed regarding FIGS. 7-10 prior to depositing the depicted first layer. An aluminum layer and associated heat treatment as depicted in and discussed regarding FIG. 7 may be applied to an Mg alloy depicted in and discussed regarding FIGS. 6 and 8-10. Alternating layers of aluminum oxide and cerium oxide as depicted in and discussed regarding FIG. 8 may be applied in addition to or as an alternative to one or more layers depicted in and described regarding FIGS. 6-7 and 9-10. One or more layers of magnesium depicted in and discussed regarding FIGS. 9-10 may be applied in addition to or as an alternative to one or more layers depicted in and described regarding FIGS. 6-8.

An Mg alloy surface or a surface of a coating layer may be texturized prior to application of a coating or additional coating. Texturizing can be done in any suitable manner. For example, texturizing can be done by sand or grit blasting with, for example, silicon oxide or aluminum oxide particles. For stent frames, the grit size is preferably 20 micrometer or less to prevent mechanical damage to the frame. The air pressure can also be adjusted to prevent mechanical damage to the frame.

Only selected coatings, coverings and treatments that can be applied to an Mg alloy or a coating that is on an Mg alloy are described herein. It will be understood that coatings in addition to those described above can be applied to an Mg alloy frame, some of which may aid in inhibiting corrosion, and thus slow biodegradation of the frame. Examples of other coatings or treatments that can be applied include thermal oxidation layers; polymers and sol-gel layers such as poly (L) lactic acid (PLLA) and octyl cyanoacrylate; and the like. Frames of stents prepared as described herein can also be coated with a drug coating, which may include a polymer or may be polymer-free. Examples of suitable drug coatings are well-known in the art.

SUMMARY OF VARIOUS ASPECTS

A number of aspects of methods and devices are disclosed herein. A summary of some selected aspects is provided below.

A first aspect is directed to a biodegradable frame for an implantable medical stent. The frame comprises a magnesium (Mg) alloy and a HF conversion coating layer on the Mg alloy. The frame may comprise an additional coating on the HF conversion coating layer. The coating additional coating may comprise alternating layers of aluminum oxide ($Al_2O_3$) and a poly(aluminum ethylene glycol) polymer (alucone). The additional coating may comprise a base layer of $Al_2O_3$, a nanolaminate of $Al_2O_3$ and alucone on the base layer of $Al_2O_3$, and a layer of alucone on the nanolaminate of $Al_2O_3$ and alucone. The total thickness of the base layer of $Al_2O_3$, the nanolaminate of $Al_2O_3$ and alucone, and the layer of alucone may be 100 nm or less.

A second aspect is directed to a biodegradable frame for an implantable medical stent. The frame comprises a magnesium (Mg) alloy core, a magnesium fluoride ($MgF_2$) layer on the core, and an additional coating on the $MgF_2$ layer. The additional coating may comprise alternating layers of aluminum oxide ($Al_2O_3$) and a poly(aluminum ethylene glycol) polymer (alucone). The additional coating may comprise a base layer of $Al_2O_3$, a nanolaminate of aluminum oxide ($Al_2O_3$) and a poly(aluminum ethylene glycol) polymer (alucone) on the base layer of $Al_2O_3$, and a layer of alucone on the nanolaminate of $Al_2O_3$ and alucone. The total thickness of the base layer of $Al_2O_3$, the nanolaminate of $Al_2O_3$ and alucone, and the layer of alucone may be 100 nm or less.

A third aspect is directed to a method for forming a biodegradable frame for an implantable medical stent. The method comprises (i) forming a frame comprising a magnesium (Mg) alloy, (ii) incubating the frame with a composition comprising hydrofluoric acid (HF) to convert a surface of the Mg alloy to a magnesium fluoride ($MgF_2$) layer, (iii) depositing a layer or aluminum oxide ($Al_2O_3$) on the $MgF_2$ layer, and (iv) depositing a nanolaminate of $Al_2O_3$ and a poly(aluminum ethylene glycol) polymer (alucone) on the $Al_2O_3$ layer. The layer of $Al_2O_3$ may be deposited by atomic layer deposition (ALD). The ALD of $Al_2O_3$ may be carried out at any suitable temperature, such as between 70° C. and 95° C. The nanolaminate of $Al_2O_3$ and alucone may be formed by depositing $Al_2O_3$ by atomic layer deposition and depositing the alucone by molecular layer deposition. Depositing of the nanolaminate may be carried out at any suitable temperature, such as between 120° C. and 130° C. The method may further comprise depositing a layer of alucone on the nanolaminate. The method may further comprise texturizing a surface of the frame prior to incubating the frame with the composition comprising HF.

A fourth aspect is directed to a biodegradable frame for an implantable medical stent. The frame comprises a magnesium (Mg) alloy core and a first layer of magnesium over the core. The frame may further comprise, for example, a layer of magnesium fluoride ($MgF_2$) between the Mg alloy core and the first layer of magnesium. The frame may further comprise a second layer of magnesium, wherein the Mg alloy core is between the first and second layers of magnesium.

A fifth aspect is directed to a method for manufacturing a biodegradable frame for an implantable medical stent. The method comprises (i) providing a tube having an inner layer of magnesium, an outer layer of magnesium, and a magnesium alloy layer between the inner and outer layers of magnesium; and (ii) laser cutting or forming the tube to produce the frame. The tube may be formed by drawing a magnesium alloy tube over a magnesium tube to form a pre-tube having the inner layer of magnesium and the magnesium alloy layer, and drawing a magnesium tube over the pre-tube to form the tube having the inner layer of magnesium, the outer layer of magnesium, and the magnesium alloy layer between the inner and outer layers of magnesium. The method may further comprise hydrofluoric acid (HF) conversion coating the magnesium alloy prior to drawing the magnesium alloy tube over the magnesium tube to form the pre-tube.

A sixth aspect is directed to a method for manufacturing a biodegradable frame for an implantable medical stent. The method comprises (i) providing a wire comprising an inner layer of magnesium alloy and an outer layer of magnesium around the inner layer; and (ii) forming or welding the wire to produce the frame. The wire may be formed by drawing a magnesium tube over a magnesium alloy wire to form the wire comprising the inner layer of magnesium alloy and the outer layer of magnesium around the inner layer. The method may further comprise hydrofluoric acid (HF) conversion coating the magnesium alloy wire prior to drawing the magnesium tube over the magnesium alloy wire.

A seventh aspect is directed to a biodegradable frame for an implantable medical stent. The frame comprises a magnesium (Mg) alloy and a coating on the Mg alloy, wherein the coating comprises a layer of aluminum oxide and a layer of cerium oxide. The coating may further comprise a hydrofluoric acid (HF) conversion coating layer on the Mg alloy. The coating may comprise multiple alternating layers of aluminum oxide and cerium oxide. One or more of the layers of the alternating layers may have a thickness of 10 nm or less. One or more of the layers of the alternating layers have a thickness of from 3 nm to 7 nm. The layer of aluminum oxide may have a thickness in a range from 5 nm to 60 nm. The layer of cerium oxide has a thickness in a range from 5 nm to 60 nm. The layer of aluminum oxide may be disposed closer to the Mg alloy than the layer of cerium oxide.

An eighth aspect is directed to a method for forming a biodegradable frame for an implantable medical stent. The method comprises (i) providing a frame comprising a magnesium (Mg) alloy, (ii) optionally incubating the frame with a composition comprising hydrofluoric acid (HF) to convert a surface of the Mg alloy to a magnesium fluoride ($MgF_2$) layer, (iii) depositing a layer of aluminum oxide on the Mg alloy or on the optional $MgF_2$ layer, if present, to produce an aluminum oxide coated frame; and (iv) depositing a layer of cerium oxide on the aluminum oxide coated frame. Depositing the layer of aluminum oxide may comprise depositing the aluminum oxide by atomic layer deposition. Depositing the aluminum oxide by atomic layer deposition may be carried out at any suitable temperature, such as at 150° C. or less. Depositing the aluminum oxide by atomic layer deposition may be carried out at any suitable temperature, such as at 100° C. or less. Depositing the layer of cerium oxide may comprise depositing the cerium oxide by atomic layer deposition. Depositing the cerium oxide by atomic layer deposition may be carried out at any suitable temperature, such as at 300° C. or less. The method may further comprise texturizing a surface of the Mg alloy.

A ninth aspect is directed to a biodegradable frame for an implantable medical stent. The frame comprises a magnesium (Mg) alloy and a coating on the Mg alloy, wherein the coating comprises a layer of aluminum and a layer of graphene. The coating may further comprise a hydrofluoric acid (HF) conversion coating layer on the Mg alloy. The coating may further comprise a layer of aluminum oxide ($Al_2O_3$). The coating may comprise a layer of aluminum, a layer of aluminum oxide on the layer of aluminum, and a layer of graphene on the layer of aluminum oxide.

A tenth aspect is directed to a biodegradable frame for an implantable medical stent. The frame comprises (i) an Mg alloy core; (ii) a layer of $Mg_{17}Al_{12}$ on the core; (iii) a layer of aluminum on the layer of $Mg_{17}Al_{12}$; (iii) an optional aluminum oxide ($Al_2O_3$) layer on the layer of aluminum; and (iv) a layer of graphene on the layer of aluminum or the optional layer of $Al_2O_3$, if present.

An eleventh aspect is directed to a method for forming a biodegradable frame for an implantable medical stent. The method comprises (i) providing a frame comprising a magnesium (Mg) alloy; (ii) optionally incubating the frame with a composition comprising hydrofluoric acid (HF) to convert a surface of the Mg alloy to a magnesium fluoride ($MgF_2$) layer; (iii) depositing a layer of aluminum on the Mg alloy or on the optional $MgF_2$ layer, if present, to produce an aluminum coated frame; and (iv) depositing a layer of graphene on the aluminum coated frame. The method may further comprise texturizing a surface of the Mg alloy. Texturizing a surface of the Mg alloy may comprise grit or sand blasting the surface. Depositing the layer of aluminum may comprise depositing the aluminum by physical vapor deposition. Depositing the layer of aluminum may be carried out at a temperature of 150° C. or less. The method may further comprise heating the aluminum coated frame at a temperature above 350° C. The heating of the aluminum coated frame may result in formation of an $Mg_{17}Al_{12}$ intermetallic between the layer of aluminum and the Mg alloy. Heating the aluminum coated frame may comprise heating in the presence of oxygen to form a layer of aluminum oxide ($Al_2O_3$) on a surface of the aluminum coated frame. The method may comprise the step of incubating the frame with a composition comprising hydrofluoric acid (HF) to convert a surface of the Mg alloy to a magnesium fluoride ($MgF_2$) layer.

A twelfth aspect is a biodegradable implantable medical device. The device comprising a magnesium (Mg) alloy and a coating on the Mg alloy. The coating comprises one or both of (i) a conversion coating that removes exposed second phases from a surface of the Mg alloy; and (ii) one or more moisture barrier layers. Non-limiting examples of suitable conversion coatings include an HF conversion coating; a conversion coating with acidic or basic solutions of $Ce^{3+}$ or $Ce^{4+}$; a conversion coating with an acidic or basic solution comprising an inorganic magnesium precipitating agent; and a conversion coating with an acidic or basic solution comprising an organic magnesium precipitating agent. Examples of inorganic magnesium precipitating agents include phosphates, silicates, permanganates, hydrotalcite, vanadates, chromates, and Rare Earth ions other than a cerium ion. Examples of organic magnesium precipitating agents include 4-(4-nitrophenylazo)-resorcinol, 8-hydroxy quinolone, and sodium dodecylbenzenesulphonate.

Examples of moisture barrier layers include a layer of: aluminum, magnesium, cerium oxide, aluminum oxide, titanium oxide, titanium ethylene glycol, titanium propylene glycol, zirconium oxide, zirconium ethylene glycol, zirconium propylene glycol, hafnium oxide, hafnium ethylene glycol, hafnium propylene glycol, aluminum fluoride, or magnesium fluoride.

Definitions

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to a product, method or the like, means that the components of the, product, method or the like are limited to the enumerated components and any other components that do not materially affect the basic and novel characteristic(s) of the composition, product, method or the like.

"Optional" or "optionally" means that the subsequently described event, circumstance, or component, can or cannot occur, and that the description includes instances where the event, circumstance, or component, occurs and instances where it does not.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

It is also noted that recitations herein refer to a component being "configured" or "adapted to" function in a particular way. In this respect, such a component is "configured" or "adapted to" embody a particular property, or function in a particular manner, where such recitations are structural recitations as opposed to recitations of intended use. More specifically, the references herein to the manner in which a component is "configured" or "adapted to" denotes an existing physical condition of the component and, as such, is to be taken as a definite recitation of the structural characteristics of the component.

EXAMPLES

A number of coating, surface modification or other processes for slowing or unifying the corrosion, and thus biodegradability, of Mg alloys for use as stent frames have been tested. Selected non-limiting examples of the processes that have been investigated will now be described.

Example 1: Combination of HF Conversion Coating and Nanolaminate

Figure 11A:
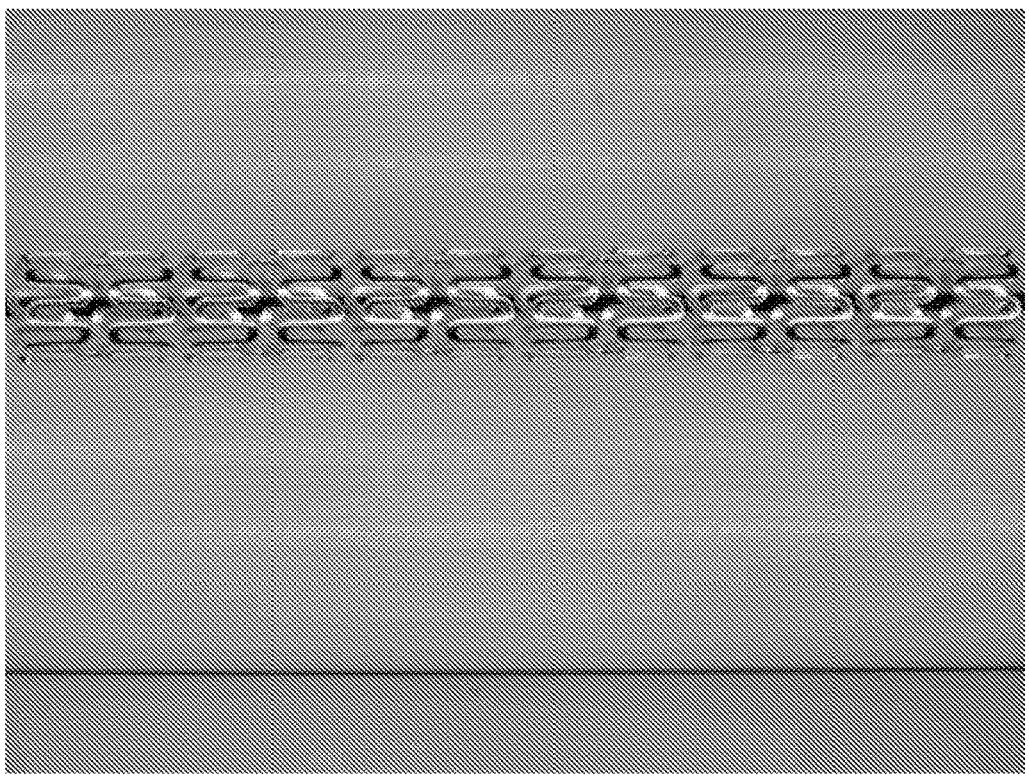
FIG. 11A is an image of a bare electropolished Mg alloy stent.
Figure 11B:
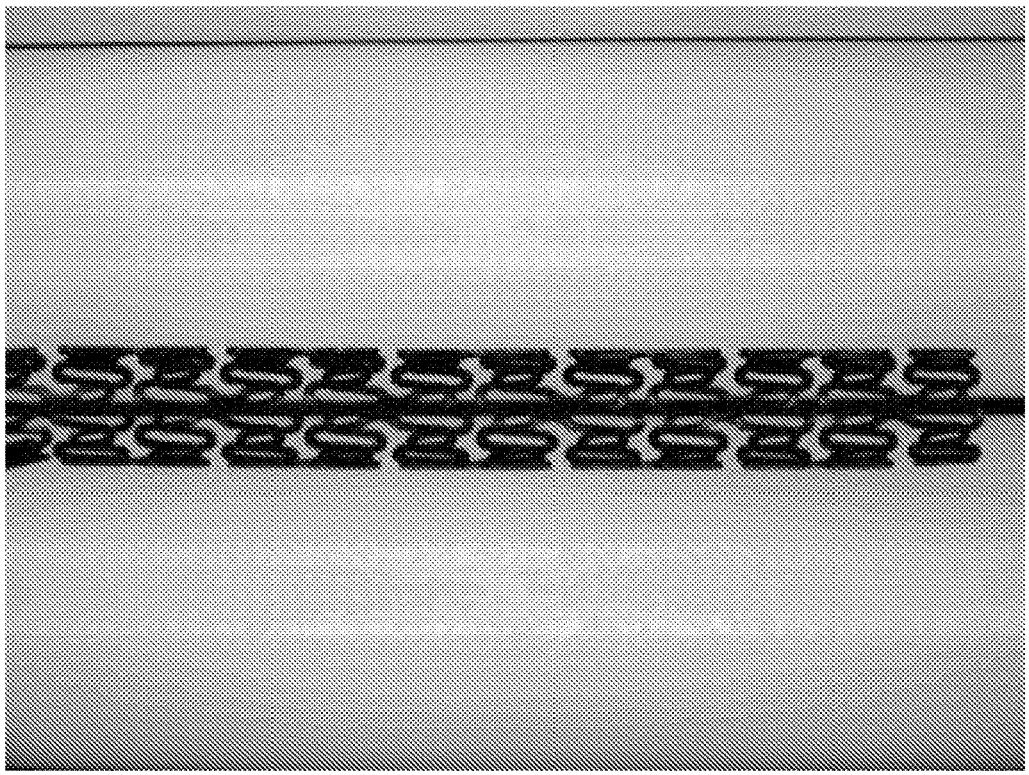
FIG. 11B is an image of an electropolished Mg alloy stent post HF treatment.

AE42 Mg alloy stents were immersed in a 49% HF solution for a 24 hour immersion time at ambient conditions to conversion coat the Mg alloy with hydrous $MgF_2$ having a thickness of about one to two microns. The resultant film was uniform and dark in appearance. Compare FIG. 11A, which is an image of a bare electropolished Mg alloy stent, to FIG. 11B, which is an image of an electropolished Mg alloy stent post HF treatment. The treatment resulted in the removal of precipitants and defects on the surface of the stent, which was shown to cause more uniform corrosion.

An aluminum oxide coating or a coating of a nanolaminate of aluminum oxide and alucone was applied to HF conversion coated AE42 Mg alloy stents, thermal oxide treated AE42 Mg alloy stents, and bare AE42 Mg alloy stents.

Thermal oxidation of AE42 Mg alloy stents was carried out as follows. Briefly, the Mg alloy stents were heated at 485° C. for 6 hours in an oxygen and argon environment or alternatively the magnesium alloy stents were heated in an oxygen and nitrogen environment.

Aluminum oxide was deposited as follows. Briefly, 100 nm of aluminum oxide was deposited at 95° C. on the stent. The stent was crimped onto a balloon catheter and then expanded to deploy before corrosion testing. For corrosion testing, the deployed stent was statically soaked in fetal bovine serum (FBS) at physiological conditions (37° C. and 5% $CO_2$) for the designated time periods. An antibiotic was also used (1 mL/30 mL of FBS) to prevent bacterial growth during the corrosion process. After the designated time period, the stents were removed from the FBS, rinsed, and cross-sectioned. The amount of metal remaining was analyzed by an area measurement.

An aluminum oxide/alucone nanolaminate was deposited as follows. Briefly, stents were first coated with a 1.2 nm thick layer of aluminum oxide via ALD at 95° C. (ten cycles of ALD). Then alucone was coated via molecular layer deposition (MLD) for 2 cycles at 95° C. Next, additional layers were coated at 120° C. as alternating layers of $Al_2O_3$ and alucone as follows: aluminum oxide at 10 cycles of ALD and alucone at 2 cycles of MLD until a final thickness of around 40 nm was reached.

Figure 12:
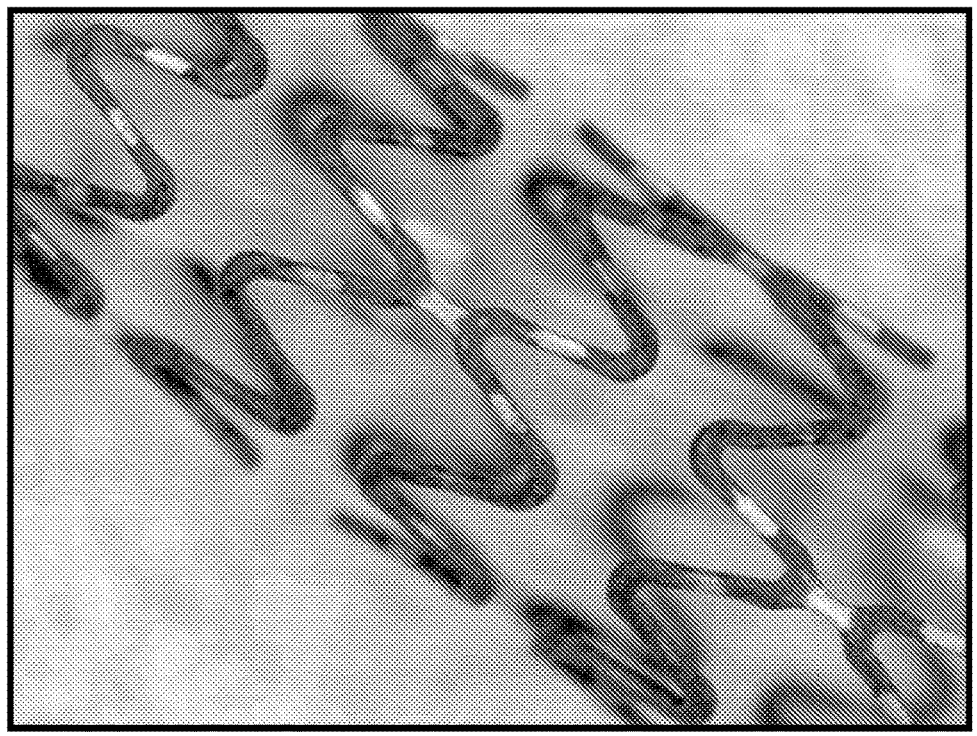
FIG. 12 is an image of a crimped and deployed magnesium alloy stent coated with a thermal oxide and $Al_2O_3$ and corroded for 4 weeks in vitro.

The stents coated with aluminum oxide only had a brittle coating that cracked upon crimping/deploying of the stent. No corrosion was observed at low-stress areas (such as mid-strut) compared to high stress areas (crown) which could be seen visually following corrosion testing (FIG. 12).

Figure 13:
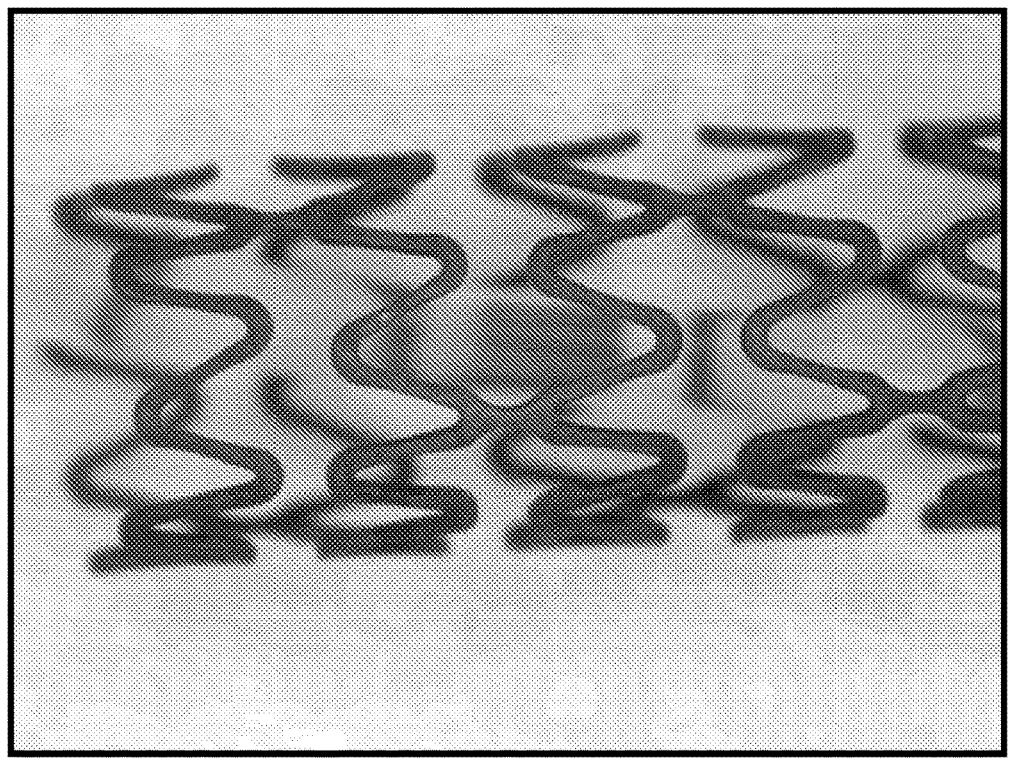
FIG. 13 is an image of a crimped and deployed magnesium alloy stent coated with $MgF_2$ and $Al_2O_3$/Alucone and corroded for 4 weeks in vitro.

In contrast, the Mg alloy stent coated with $MgF_2$ and $Al_2O_3$/alucone subjected to 4 weeks of corrosion testing showed no visible signs of corrosion (FIG. 13).

Figure 14:
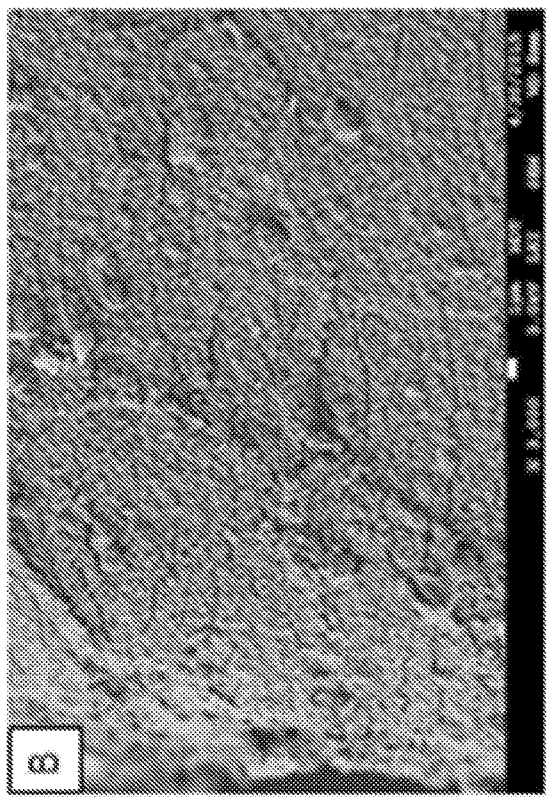
FIG. 14 shows scanning electron microscope images of stents. Panel A shows $Al_2O_3$/Alucone on a bare stent after crimping and deploying. Panel B shows a thermally oxidized stent after crimping and deploying. Panel C shows a $MgF_2$ stent after crimping and deploying.
Figure 14:
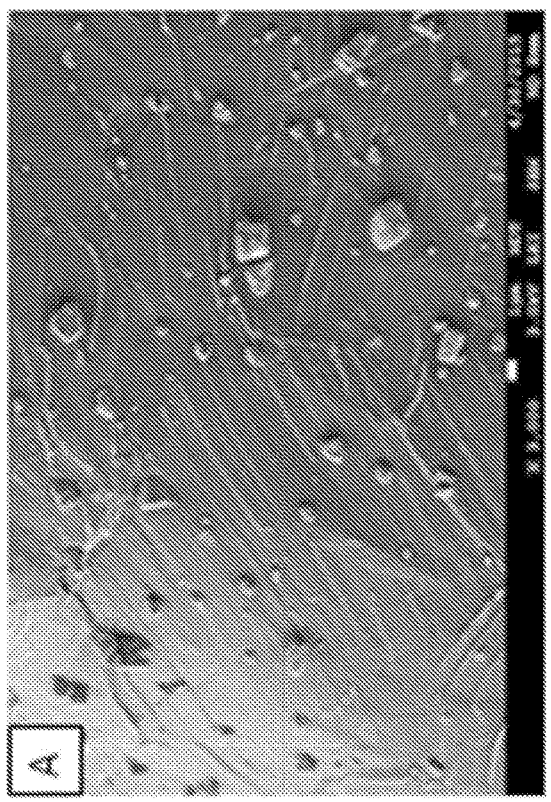
Figure 14:
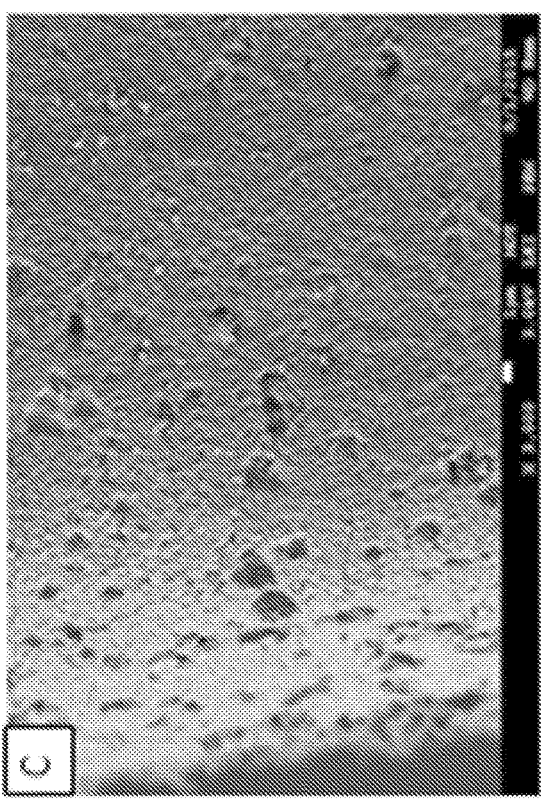

The unique combination of an HF conversion coating as the base followed by an $Al_2O_3$/Alucone nanolaminate results in slow and uniform corrosion that cannot be achieved with either coating alone. The HF coating is responsible for the uniform corrosion of the base metal along with improving adhesion of the ALD/MLD nanolaminate. Compare FIG. 14 Panels A-C, which show SEM images of $Al_2O_3$/Alucone on (Panel A) bare, (Panel B) thermally oxidized and (Panel C) $MgF_2$ stents after crimping and deploying.

Figure 15:
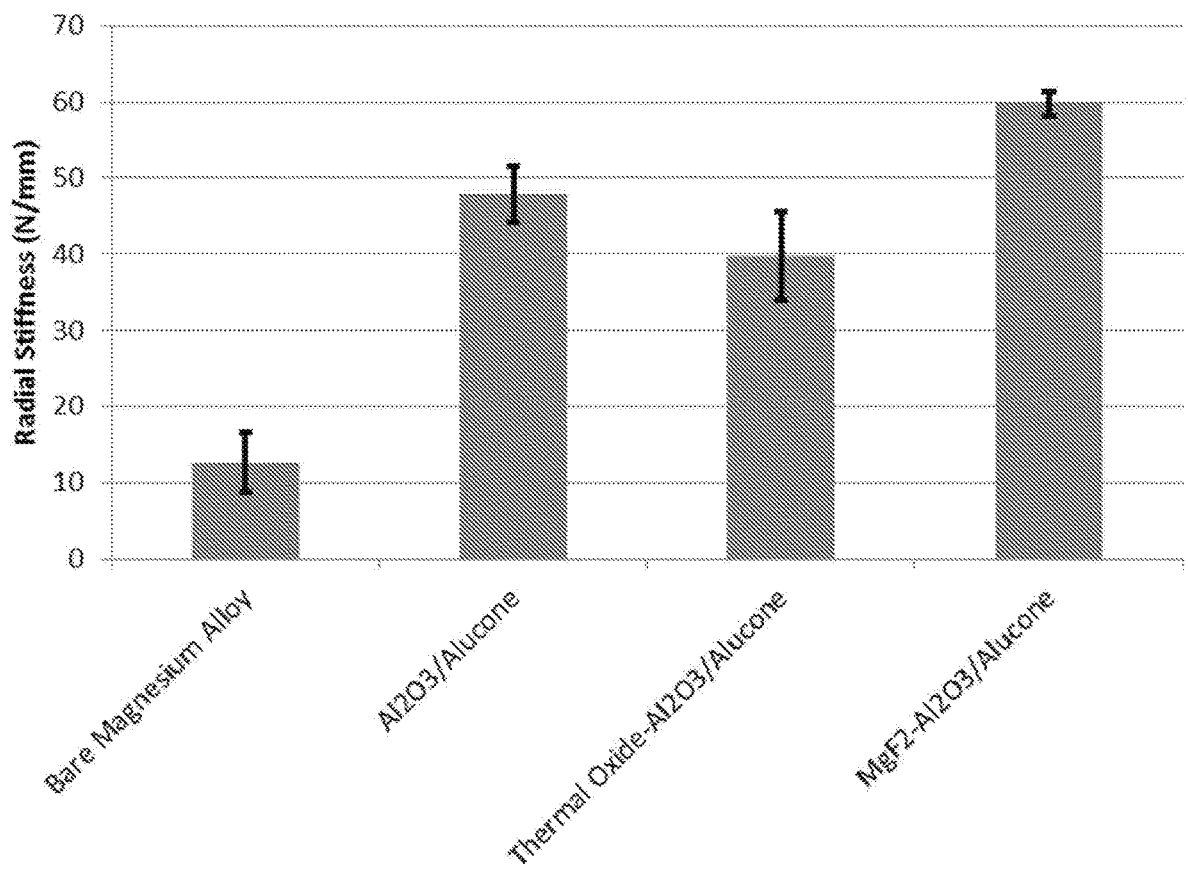
FIG. 15 is a bar graph showing radial stiffness values after 4 weeks of in vitro corrosion of bare magnesium stents, and bare, thermally-oxidized, or HF treated stents with $Al_2O_3$/alucone coating.

Radial stiffness of resulting stents was also tested following 4 weeks of corrosion testing. For radial stiffness testing the force to compress the stent to a given diameter was measured. Results are shown in FIG. 15, which indicates that the ALD/MLD aluminum oxide/alucone nanolaminate has a desired combination of flexibility and barrier properties to resist fracturing during the crimp and deploy processes and effectively keep water and electrolytes away from the magnesium surface. Radial stiffness of thermal oxide treated Mg alloy stents coated with alternating layers of aluminum oxide and alucone was substantially lower than radial stiffness of the HF conversion coated Mg alloy stents coated with alternating layers of aluminum oxide and alucone (see, e.g., FIG. 15). Coating an aluminum oxide/alucone nanolaminate on a bare Mg alloy stent similarly produced stents having reduced radial stiffness relative to HF conversion coated Mg alloy stents coated with the aluminum oxide/alucone nanolaminate (see, e.g., FIG. 15).

Figure 16:
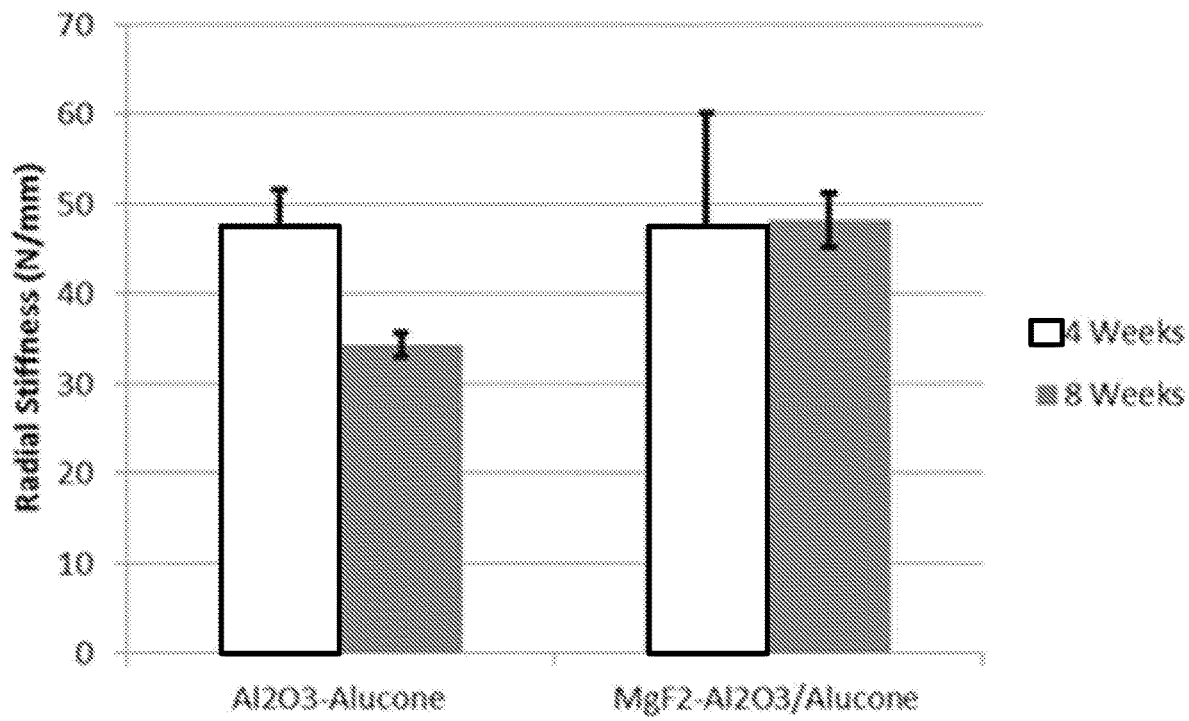
FIG. 16 is a bar graph comparing radial stiffness values after 4 and 8 weeks of corrosion testing of differently coated stents.

Referring now to FIG. 16, radial stiffness results after 8 weeks of corrosion testing are shown. The stents were crimped and deployed before corrosion (their use condition) and then tested post-corrosion to measure radial stiffness. As shown in FIG. 16, after 4 weeks of corrosion the radial stiffness of aluminum oxide/alucone coated Mg alloy stents and $MgF_2$—$Al_2O_3$/alucone coated Mg alloy stents was similar. However, after 8 weeks of in vitro corrosion the $MgF_2$—$Al_2O_3$/alucone coated Mg alloy stents maintained their radial stiffness (indicating no corrosion), while the radial stiffness of aluminum oxide/alucone coated Mg alloy stents decreased.

The fraction of metal remaining in the stents after 4 and 8 weeks of corrosion testing was determined. The stents were cross-sectioned at three locations across the stent length. Images of each strut were taken at high magnification. Then the area of the metal and the area of the corroded material were measured and a ratio of metal/total area was calculated to determine the fraction of metal remaining. Higher fractions of metal remaining correspond to better corrosion resistance.

Figure 17:
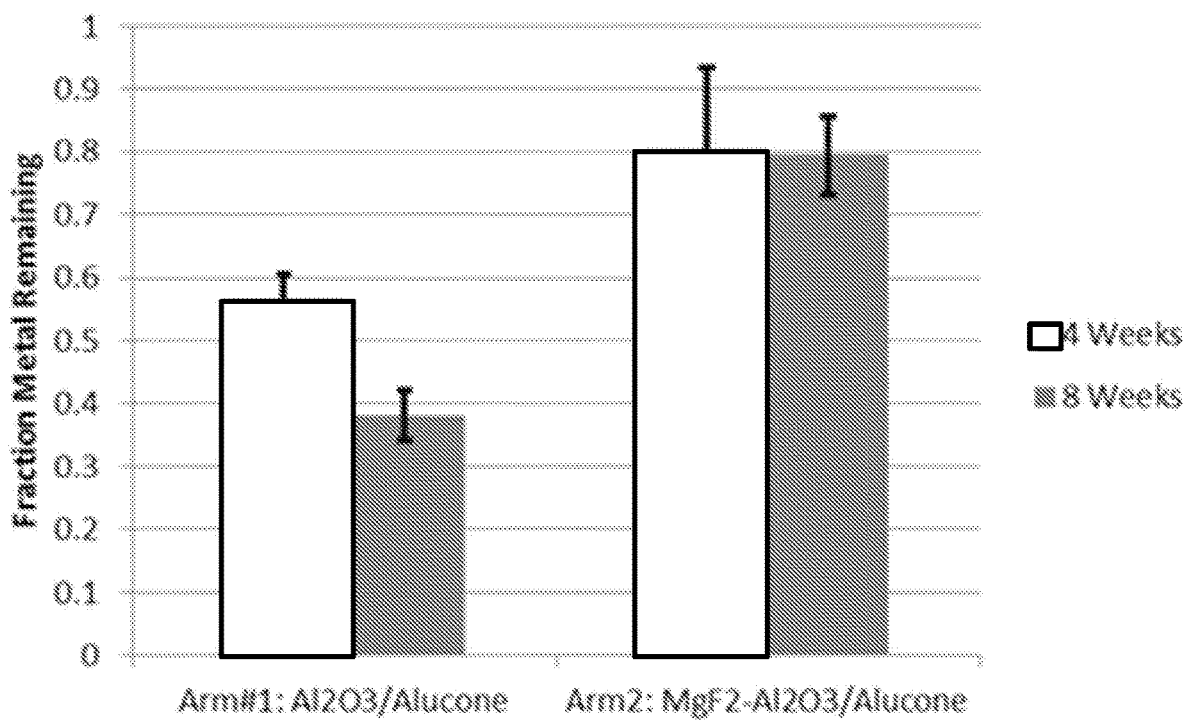
FIG. 17 is a bar graph comparing the fraction of metal remaining after 4 and 8 weeks of corrosion testing of differently coated stents.

Results are presented in FIG. 17, which indicates that substantially more corrosion appears to be occurring in the aluminum oxide/alucone coated Mg alloy stents than in the $MgF_2$—$Al_2O_3$/alucone coated Mg alloy stents.

As shown from the results above, the unique combination of the uniform corrosion provided by the HF conversion coating with the flexibility and barrier properties of the $Al_2O_3$/alucone coatings results in slow and uniform corrosion across the stent surface and results in high strength/radial stiffness. These results indicate that $Al_2O_3$/alucone coated HF-conversion coated Mg alloy stents are good candidates as extended life biodegradable stents.

Example 2: Aluminum Oxide and Cerium Oxide Coated Magnesium Alloy Stents

Figure 18:
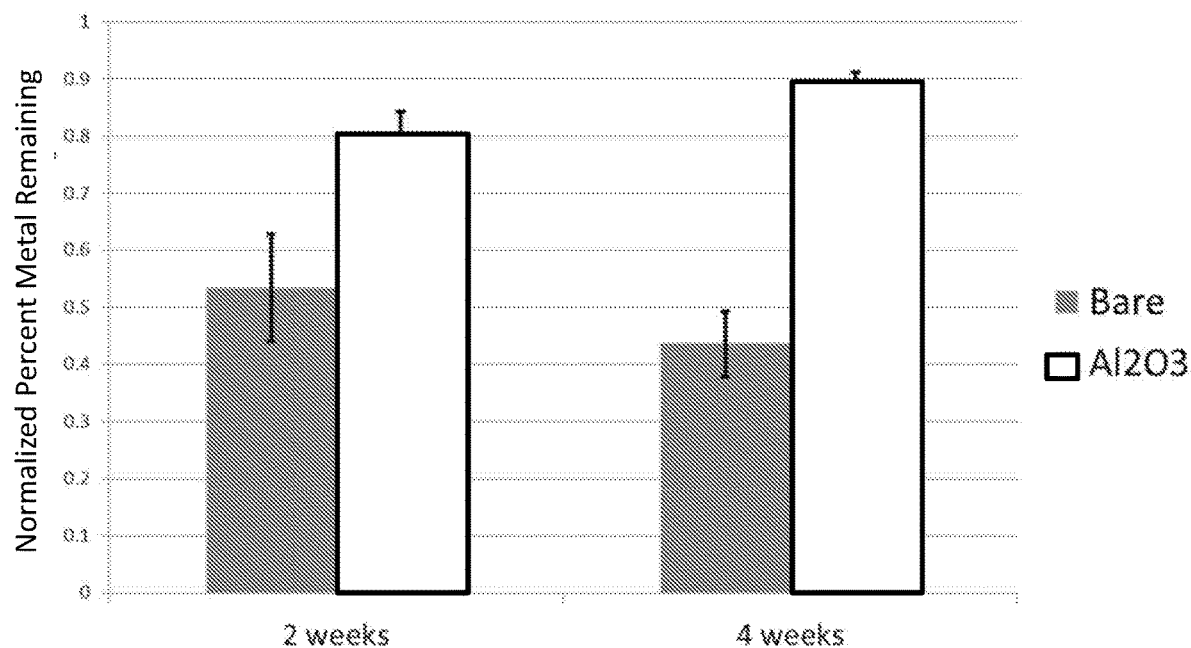
FIG. 18 is a bar graph showing the percent metal remaining of bare Mg alloy and aluminum oxide coated Mg alloy samples after 2 weeks and 4 weeks of corrosion testing.

Bare Mg alloy (AE42) and aluminum oxide coated Mg alloy (AE42 with 100 nm of aluminum oxide deposited by ALD at 95° C.) samples were subjected to in vitro corrosion testing, generally as described above regarding Example 1. The percent metal remaining in such stents after 2 weeks and 4 weeks of corrosion testing are shown in FIG. 18. As shown, atomic layer deposition (ALD) of aluminum oxide ($Al_2O_3$) on magnesium alloy can be an effective way to slow corrosion (FIG. 18). However, when placed on a stent that is crimped and deployed and subjected to fatigue in vivo, aluminum oxide coatings may not sufficiently slow corrosion of the Mg alloy to allow effective stent function for a desired amount of time. See, for example, FIG. 12 and associated discussion above in Example 1.

Figure 19:
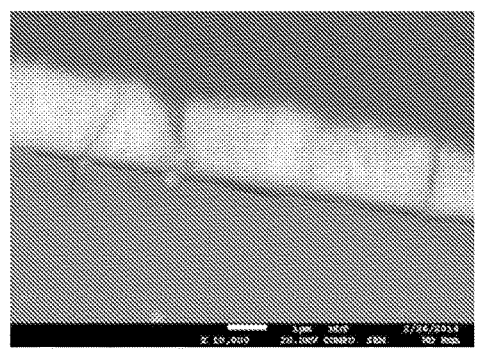
FIG. 19 is an image of a cerium nitrate conversion coating on a magnesium alloy.

Cerium has also been shown in a variety of literature to act as a corrosion inhibitor for magnesium alloys. However, cerium nitrate conversion coatings are flaky and do not adhere well to the surface of Mg alloys (FIG. 19). For cerium nitrate conversion coating, AE42 stents were immersed in 0.05-0.005M solutions of cerium nitrate in water for a few minutes up to a few hours while the solution is being mixed.

An ALD layer incorporating $CeO_2$ may have a self-healing capacity desired for corrosion protection while maintaining a uniform and thin structure, which is not possible with current cerium nitrite conversion coating processed.

Alternating ALD layers of aluminum oxide and cerium oxide may prove particularly beneficial.

Thus, systems, devices and methods for COATING FOR UNIFORM SLOW BIOCORROSION OF MAGNESIUM ALLOYS are described. Those skilled in the art will recognize that the preferred embodiments described herein may be altered or amended without departing from the true spirit and scope of the disclosure, as defined in the accompanying claims. In the detailed description above several specific embodiments of implantable medical devices and systems and coating methods are disclosed. It is to be understood that other embodiments are contemplated and may be made without departing from the scope or spirit of the present disclosure. The detailed description, therefore, is not to be taken in a limiting sense. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents.

The invention claimed is:

1. A biodegradable frame for an implantable medical stent, the frame comprising:
   a magnesium (Mg) alloy core;
   a conversion coating that removes exposed secondary phases from a surface of the Mg alloy; and
   a layer of pure magnesium over the conversion coating.

2. The biodegradable frame of claim 1, wherein the conversion coating comprises a conversion coating selected from the group consisting of:
   a hydrofluoric acid (HF) conversion coating; a conversion coating with acidic or basic solutions of $Ce^{3+}$ or $Ce^{4+}$;
   a conversion coating with an acidic or basic solution comprising an inorganic magnesium precipitating agent; and
   a conversion coating with an acidic or basic solution comprising an organic magnesium precipitating agent.

3. The biodegradable frame of claim 2, wherein the conversion coating comprises a conversion coating with an acidic or basic solution comprising an inorganic magnesium precipitating agent, and wherein the inorganic magnesium precipitating agent is selected from the group consisting of a phosphate, a silicate, a permanganate, a hydrotalcite, a vanadate, a chromate and a Rare Earth ion other than a cerium ion.

4. The biodegradable frame of claim 2, wherein the conversion coating comprises a conversion coating with an acidic or basic solution comprising an organic magnesium precipitating agent, and wherein the organic magnesium precipitating agent is selected from the group consisting of 4-(4-nitrophenylazo)-resorcinol, 8-hydroxy quinolone, and sodium dodecylbenzenesulphonate.

5. The biodegradable frame of claim 2, wherein the conversion coating comprises an HF conversion coating.

6. A stent comprising the biodegradable frame of claim 1.

7. A biodegradable tubular frame for an implantable medical stent, comprising:
   a magnesium (Mg) alloy layer;
   a first layer of pure magnesium;
   a second layer of pure magnesium, and
   a first conversion coating layer on the Mg alloy layer;
   wherein the Mg alloy layer is between the first and the second layers of pure magnesium, and
   wherein the first conversion coating layer is between the Mg alloy layer and the first layer of pure magnesium, and wherein the first conversion coating layer removes exposed secondary phases from a surface of the Mg alloy layer.

8. The biodegradable tubular frame of claim 7, wherein the first layer of pure magnesium defines an inner layer of the tubular frame.

9. The biodegradable tubular frame of claim 8, wherein the second layer of pure magnesium defines an outer layer of the tubular frame.

10. The biodegradable tubular frame of claim 7, wherein the second layer of pure magnesium defines an outer layer of the tubular frame.

11. The biodegradable tubular frame of claim 7, further comprising a second conversion coating layer on the Mg alloy layer, wherein the second conversion coating layer is between the Mg alloy layer and the second layer of pure magnesium, and wherein the second conversion coating layer removes exposed secondary phases from a surface of the Mg alloy layer.

12. A stent comprising the biodegradable tubular frame of claim 7.

13. A biodegradable tubular frame, for an implantable medical stent, comprising:
   a magnesium (Mg) alloy layer;
   a conversion coating layer on the Mg alloy layer;
   a first layer of pure magnesium; and
   a second layer of pure magnesium;
   wherein the Mg alloy layer is between the first and the second layers of pure magnesium, and
   wherein the conversion coating layer is between the Mg alloy layer and the second layer of pure magnesium, and wherein the conversion coating layer removes exposed secondary phases from a surface of the Mg alloy layer.

* * * * *